(12) United States Patent
Rossi et al.

(10) Patent No.: US 10,019,430 B2
(45) Date of Patent: Jul. 10, 2018

(54) SYSTEM AND METHOD FOR AUTOMATICALLY FILLING OUT FORMS

(71) Applicants: Thomas Ralph Rossi, Villa Park, CA (US); John Anthony Capone, Mission Viejo, CA (US); Dan Gerard Fitzgerald, Laguna Hills, CA (US)

(72) Inventors: Thomas Ralph Rossi, Villa Park, CA (US); John Anthony Capone, Mission Viejo, CA (US); Dan Gerard Fitzgerald, Laguna Hills, CA (US)

( * ) Notice: Subject to any disclaimer, the term of this patent is extended or adjusted under 35 U.S.C. 154(b) by 0 days.

(21) Appl. No.: 15/592,505

(22) Filed: May 11, 2017

(65) Prior Publication Data

US 2017/0249592 A1 Aug. 31, 2017

Related U.S. Application Data

(63) Continuation-in-part of application No. 14/617,355, filed on Feb. 9, 2015.

(51) Int. Cl.
| | |
|---|---|
| *G06F 17/00* | (2006.01) |
| *G06F 17/24* | (2006.01) |
| *G06F 17/22* | (2006.01) |
| *G06Q 10/10* | (2012.01) |
| *G16H 10/60* | (2018.01) |
| *G16H 10/65* | (2018.01) |

(52) U.S. Cl.
CPC ........ *G06F 17/243* (2013.01); *G06F 17/2205* (2013.01); *G06F 17/248* (2013.01); *G06Q 10/10* (2013.01); *G16H 10/60* (2018.01); *G16H 10/65* (2018.01)

(58) Field of Classification Search
CPC ... G06F 17/243; G06F 17/2205; G06F 17/248
See application file for complete search history.

(56) References Cited

U.S. PATENT DOCUMENTS

| | | | | |
|---|---|---|---|---|
| 6,199,079 B1* | 3/2001 | Gupta | ................ | G06F 17/2247 |
| | | | | 707/999.006 |
| 6,490,601 B1* | 12/2002 | Markus | ................ | G06F 17/243 |
| | | | | 705/80 |
| 7,660,779 B2 | 11/2005 | Goodman | | |

(Continued)

*Primary Examiner* — Cesar Paula
*Assistant Examiner* — David Faber

(57) ABSTRACT

The invention comprises a system and method for storing consumers' data and automatically filling out forms by sending this information to merchants, allowing users to complete forms and exchange information much faster than could be done by hand. The invention includes an online repository of personal information, and a method to provide easily accessible, secure, sharable data. The invention includes a central repository for forms data, through which merchants can build their own applications, interact with other users, and avoid the inconvenience of filling out forms. The invention will only release the data, to a merchant, that is needed to complete a specific form. A user can send and receive form-related data during different transactions. Consumers will create and maintain a web-based Online Profile (OP) with data that merchants can access, after authentication, via a device with web access. The invention reduces identity theft, via a record of all a consumer's transactions.

23 Claims, 9 Drawing Sheets

(56) References Cited

U.S. PATENT DOCUMENTS

| | | | | |
|---|---|---|---|---|
| 7,062,258 B1* | 6/2006 | Sini | ............ | G06F 17/243 455/414.1 |
| 7,200,578 B2* | 4/2007 | Paltenghe | ............ | G06F 21/6209 705/1.1 |
| 7,334,184 B1* | 2/2008 | Simons | ............ | G06F 17/30867 715/234 |
| 9,069,745 B2 | 7/2008 | Jacobsen | | |
| 8,868,641 B2 | 11/2010 | Bolnick | | |
| 8,850,304 B2 | 8/2011 | Ye | | |
| 8,719,690 B2 | 9/2011 | Perelman | | |
| 9,081,756 B2 | 9/2011 | Maxwell | | |
| 9,081,854 B2 | 1/2014 | Ulanov | | |
| RE45,371 E* | 2/2015 | Simons | ............ | 715/224 |
| 9,262,392 B2* | 2/2016 | Nash | ............ | G06F 17/243 |
| 9,881,331 B2* | 1/2018 | Zises | ............ | G06Q 50/12 |
| 2001/0027439 A1* | 10/2001 | Holtzman | ............ | G01R 33/50 705/39 |
| 2002/0062342 A1* | 5/2002 | Sidles | ............ | G06F 17/243 709/203 |
| 2002/0107755 A1* | 8/2002 | Steed | ............ | G06F 17/243 705/26.1 |
| 2005/0183003 A1* | 8/2005 | Peri | ............ | G06F 17/243 715/226 |
| 2011/0078770 A1* | 3/2011 | Nash | ............ | G06F 17/243 726/5 |
| 2012/0084199 A1* | 4/2012 | Stone | ............ | G06F 17/243 705/39 |
| 2012/0136756 A1* | 5/2012 | Jitkoff | ............ | G06F 17/30905 705/27.1 |
| 2013/0097479 A1* | 4/2013 | Zavaleta | ............ | G06F 17/243 715/222 |
| 2014/0298151 A1* | 10/2014 | Fitzpatrick | ............ | G06F 17/243 715/226 |
| 2016/0162460 A1* | 6/2016 | Nash | ............ | G06F 17/243 715/226 |
| 2017/0300914 A1* | 10/2017 | Li | ............ | G06Q 20/3276 |

* cited by examiner

15 ▶ [V] NAME
JOHN SMITH

15 ▶ [V] ADDRESS
999 OCEAN AVENUE

15 ▶ [V] CITY          STATE
NEW YORK    NY

15 ▶ [V] ANUAL INCOME
$70,000

15 ▶ [V] SOCIAL SECURITY NUMBER
111-11-1111

15 ▶ [V] OWN / RENT HOME
OWN

15 ▶ [V] PRESENT VECHICLE
2010 HONDA CIVIC

15 ▶ [V] CURRENT BANK
CITIBANK

15 ▶ [V] OTHER LOANS
MORTGAGE $300,000

15 ▶ [V] CARRENT SAVINGS
$30,000

15 ▶ [V] YEARS IN RESIDENCE
10

FIG. 2

SYSTEM AND METHOD FOR AUTOMATICALLY FILLING OUT FORMS

DESCRIPTION OF THE RELATED ART

Individuals often have to fill out forms when they make a purchase, visit a doctor, open a new bank account, or engage in thousands of other activities. These forms are usually paper-based, though some forms are electronic. A consumer will spend a significant amount of time each year, filling out forms. Many of these forms ask for certain common information, including an individual's name, phone number, and address. Other forms might ask for additional, more specific, information, such as a list of an individual's past residences, or, in the case of a form for opening a brokerage account, a list of the individual's other brokerage accounts. A hospital or medical provider might want to know about a patient's medical history before treating the patient. The type of information that the form will ask for is related to the needs of the entity that created the form. Filling out forms is repetitive and time-consuming. There is also the possibility that paper-based forms may become lost, or otherwise unavailable, and paper-based forms require storage. An organization or merchant may also sometimes simply run out of all copies of specific paper-based forms. Some merchants, such as insurance companies that have set up booths at a street fair may simply have no physical place to put paper forms, and therefore be unable to use them, or to acquire customers' information easily. This problem is more urgent because merchants of this sort may need particular, specialized data from consumers.

Merchants can use the information in the forms filled out by consumers to keep track of the consumers' identities, needs and wants. It is far easier for a merchant to do this if the information in the forms filled out by consumers is already in a computer-readable format. In this format the forms database can be automatically replicated for redundancy whereas paper files could be lost or destroyed.

The data entry transfer from manual forms to computerized data storage is very time consuming, costly, and raises the possibility of human error. These errors are sometimes a result of illegible handwriting from a consumer, or errors in data entry. A consumer, who is asked to fill out a form, might sometimes not remember, or have readily available, all of the information that the form requires. For example, a consumer might not remember all of the street numbers associated with his or her past addresses, or the account numbers of all his or her brokerage accounts.

Some organizations, such as an automobile dealership trying to finance a customer's automobile purchase, may require much more information on their forms than other organizations, such as a restaurant trying to keep track of its customers' identities.

When a person fills out forms, he or she will often have to include some of the same types of information on many different forms. Organizations of the same type will tend to also all request certain kinds of information from a consumer, though some will require additional information as well. For example, all banks will require certain kinds of information from a person who wants to open an account, but some banks will require other information in addition to this.

Filling out forms is time consuming, and slows down numerous tasks, such as shopping and visiting healthcare practitioners. An individual's life can be placed in danger if he or she must spend a great deal of time filling out forms in a hospital before actually seeing a doctor or nurse. The filling out of forms will delay the individual from seeing the doctor or nurse. The hospital will also have to process the forms, which will also delay the individual from seeing the doctor or nurse. Even when organizations offer a digital interface to collect data, like an iPad or other tablet, the individual must fill out the forms by typing the data into the digital interface. The present invention would allow the data to be auto-populated via electronic data transfer rather than having to type all the data into the specific form offered. The present invention therefore offers advantages over prior practices in speed of input, and lack of errors and omissions.

A person making a purchase from a department store or other store will often be offered a credit card or loyalty card affiliated with the store if he or she fills out an application form and qualifies for the card. Groceries and other businesses also often offer "loyalty programs" by which a consumer may purchase things for a lower price if he or she fills out an application and signs up for a loyalty card. The types of information required on these forms are usually of a standardized nature, including certain specific items.

Many court forms also require certain types of repetitive data, such as a consumer's name and address.

Some browsers or websites save a consumer's information, including address and payment information, so that when the consumer logs on to the same website again, the information will be present on the website. However, the consumer must still input this information into the website the first time he or she visits the website or sets up the browser. This is also time-consuming, and again, the consumer might not have all the information that he or she needs readily available. Each company website must also design their own software-based storage system and their own software-based electronic forms. This is costly for merchants.

A preferable scenario would be for the consumer to only need to fill out one form, to have the information in the form stored in a centralized, secure place, and then to quickly, easily and electronically send some or all of the information within the form to merchants as needed. The merchants would then automatically input the information into their own forms, and have the information available to print out or to store or utilize electronically. This also eliminates the problem that a consumer might not know some of the data required to fill out a form, when he or she fills out the form. In our preferred scenario, the consumer will have already placed the information in the one form, stored in a centralized, secure place, and so the consumer will not need to remember all of this information when the consumer sends the relevant data to the merchant. Ideally, merchants should have their own software applications, that interact with the central data repository and place a consumer's data desired by the merchant, into the merchant's forms. To protect a consumer, the merchant should only have access to the parts of the consumer's Online Profile (OP) information that are relevant to the merchant's business. For example, a financial institution does not usually need access to a consumer's medical information. However, the consumer should be able to choose which information the merchant will have access to, so that, if for some reason a merchant wants to access information that similar merchants would not usually access, the consumer should be able to grant the merchant permission to access this information.

A solution has not yet been found, that is digitally secure, ubiquitous, universally accessible and includes the information that a user might need to fill into many different types of forms, through which the user can select the type of information that goes into a merchant's form quickly and conveniently, without a large amount of repetition. This solution should preferably allow the consumer to choose which specific forms data is released to the merchant, because different types of merchants may require different types of forms data. This solution also should include the capability for the merchant's forms to be quickly populated with the consumer's forms data, so that these populated forms can be printed out, if desired.

INVENTIONS OF THE PRIOR ART

The following inventions have been made, but these inventions do not accomplish the necessary tasks for the present invention, which are discussed above.

U.S. Pat. No. 9,069,745 by Jacobsen describes a method, using computers, of 1. Receiving entry identifying data and form identifying data to identify a sequence of one or more electronic forms, the sequence including a target electronic form having a form element. 2. Determine an entry identifier, based on the entry-identifying data. 3. Select form element identifying data corresponding to the form element within the target electronic form. 4. Selecting an entity attribute identifier based on the target form identifying data and the form element identifying data and selecting an entity attribute based on the entity attribute identifier and the entity identifier. 6. Create form-filling instructions operable to cause a machine to automatically associate the entity attribute value with the form element. 7. Repeat steps 5 and 6 if there are more form elements to be processed in sequence. 8. Transmit all form-filling instructions to remote machine.

However, the present invention is different from Jacobsen's invention because the present invention includes many subcategories of data stored in an Online Profile (OP) which a consumer can use to fill out forms. The present invention will only transmit forms data within some of these subcategories of data to the merchant, the subcategories that a consumer wishes to transmit to that merchant. The consumer also has the ability to custom-select and block some types of data in each subcategory of data that is sent to a merchant. This is especially useful when this particular data is not needed by that merchant. The present invention does not utilize the same steps as Jacobsen's invention. For example, most embodiments of the present invention do not utilize anything similar to Jacobsen's step 6, above. Our present invention also includes the possibility of having a preloaded forms database, or an onsite forms database, created by the merchant. This does not seem to be present in Jacobsen's invention. Our invention also does not utilize anything similar to step 3 of Jacobsen's invention above. Our invention also includes the possibility that the merchant can display an image to a consumer, which the consumer can then video-capture with his or her cellular phone. This image will be converted to a data stream, which will then be transmitted to a server. The form that the consumer is being asked to fill out will then be determined, based on the content of the data stream, and then consumer's pre-saved forms data will then be matched to the form that the consumer is being asked to fill out. Jacobsen's invention contains nothing similar to this.

U.S. Pat. No. 9,081,756 by Maxwell et. al. of Microsoft seems to be concerned with the idea of having to fill out computer-based forms over and over again. The patent describes a method and system of populating an electronic form with previously stored data, based on recognizing the data fields that need to be populated, and then determining whether the form type is of a type recognized by a form completion program and populating the fields in that form with the stored data.

Maxwell's patent does not include any information about the form completion program itself, so our invention includes software components that Maxwell's invention simply lacks. Our invention also is based partially on the idea of having a series of digitally protected "tiers" of data, which any merchant should be able to access, with permission from the consumer. This is more versatile than Maxwell's invention, and can be used in more situations.

U.S. Pat. No. 9,081,854 by Ulanov et. Al. describes a method for classifying large numbers of documents into hierarchies, by scanning the documents, using a K-means algorithm to determine appropriate clusters of the documents, and then testing characteristics of the clustering system to determine if it needs to be repeated, or is accurate. Ulanov's patent is focused on creating hierarchies of documents once the documents are created and the information in the documents is readily available. Our invention, by contrast, is focused on having digitally secure categories of information needed to create documents, (forms), so our invention is different from that of Ulanov.

U.S. Pat. No. 8,868,641 by Bolnick discusses methods for storing information from a plurality of accounts that a user may have online, and then, in response to a request for information from one account, also including information from the user's other accounts after a determination is made that the first account is part of a group which includes the user's other accounts. Our invention is different from that of Bolnick because our invention is oriented specifically towards storing the information that might be required for different types of forms, and using this information to create new forms.

U.S. Pat. No. 8,850,304 by Ye has as its goal: "The present invention generally relates to systems and methods for managing and completing electronic forms, and more particularly, to a system and method for mapping healthcare administrative forms to a common object model for automating the completion of such forms." Our data mapping system is different from Ye's, however.

U.S. Pat. No. 8,719,690 by Perelman includes a method of aggregating electronic forms into one group. One version of the invention picks up metadata specific to documents of a certain type to determine that they are of that type, and should be aggregated together. However, this invention is different from the current invention, because the current invention also includes an online central system that a merchant can use, in an organized fashion, to get the information needed to fill out the merchant's forms, and fill these forms out automatically. Perelman's patent does not have this.

U.S. Pat. No. 7,660,779 involves an invention that uses databases to determine what is needed to autocomplete forms, but does not involve the series of tiers containing data, which is part of the present invention. The present invention also offers a more complete solution for consumers who may need to fill out all kinds of forms, including the forms that might be required by governments and businesses. The present invention is also designed to be easy and cheap to use, so that consumers can use it with "smart phones", tablets, and other computer technology that can access the internet. Our invention also includes security aspects, such as allowing a merchant to access some of a consumer's forms data only after the merchant has verified its identity (In addition to authenticating itself for the transaction).

SUMMARY OF THE INVENTION

Term Numbers

Different embodiments of the invention involve the following parts, referred to by the following numbers:

Consumer device (1). Consumer program (2). Transaction listener (3). Online Profile (OP) (4). Tier (5). Transaction ID (6). Forms Signer (7). Notification Service (8). Forms data storage (9). Transaction data storage (10). Form ID code (11). Barcode Matrix form ID code (12). Transaction code (13). Forms data values (15). Central Server (16). Request service (17). Merchant interface (18). External transaction identifier (19). Pre-loaded forms database (20).

Central Program (21). On-site forms database (22). Offline forms transposer (23). Consumer response code (24).

Definitions

For purposes of this application, a "consumer" will be a person or entity who has entered forms data into the invention, to be stored to be released to other entities in the future. Consumers will generally be individuals, but could also be other entities in some embodiments of the invention, such as companies or families. A "merchant" will be a person or entity who accesses information that has been placed in the invention by consumers. For purposes of this application, a "merchant" does not have to be an actual merchant, but can be any entity which needs consumers to fill out forms, for example, a hospital or a government agency will also count as a "merchant" for purposes of this application. A "tier" refers to a group of types of information that a consumer might allow a merchant to receive. Tiers will, in most embodiments, be numbered, so that their position relative to each other can be easily determined, but this is not a necessary feature of tiers. Tiers can also have titles, for example, "brokerage account information". Information which is more specific to the individual, and which the individual wants to keep more secret, would usually be in a "higher-numbered" tier. For example, information about the consumer's bank accounts might be in tier 5, while information about the consumer's phone number might be in tier 1. Information in higher-numbered tiers is viewable to fewer merchants in most embodiments of the invention, because in most embodiments of the invention, a merchant who has access to one tier of a consumer's forms data will have access to all lower-numbered tiers of forms data, but not necessarily to higher-numbered tiers of forms data. For example, a consumer might have all information about his medical history in one tier, and have information about his name, address, phone number, and email address in a lower tier. The first embodiment of the invention will have a hierarchy of tiers, with some being designated as higher, and some being designated as lower, for example, "Tier 1, Tier 2", etc. It is not essential to the invention for specific types of information to be classified in specific tiers, however, consumers will find it useful for specific types of potentially sensitive information to be classified in specific, higher-numbered tiers. It is also not necessary to the invention for the tiers to be hierarchical. There may be several tiers that are equal in priority. In addition, it is not necessary to the invention for a merchant who has access to one tier of a consumer's forms data to have access to all lower tiers of the consumer's forms data. However, it is the inventors' judgment that an embodiment of the invention that incorporates hierarchical tiers where a merchant who has access to one tier of a consumer's information has access to all lower tiers, will be most useful to consumers. These are characteristics of the first embodiment.

Most embodiments, of the invention, will include a merchant interface (18) and a consumer program (2). These two software components of the invention will include, in most embodiments of the invention, lists of the types of information that are included in each tier. A consumer can review these lists, if desired. This will make it easier for a consumer to track whether or not a merchant is asking for information that the merchant probably does not need.

A consumer device (1) can be a desktop computer, laptop computer, "smart phone", tablet, or any other device capable of connecting to the internet and performing the necessary functions of the consumer device described in this application. The consumer program (2) is an "app", downloaded onto the consumer device (1), that allows the consumer to connect to the central server (16) or central program (21) or other location where the Online Profile (4) is located, and to allow the consumer to give commands to allow forms data to be released from the forms data storage (9).

The forms data values (15) are the different locations where data appears after it has been placed in a form. For example, in a typical form, some of the forms data values will be the locations where the consumer places the name and the address of the consumer filling out the form.

A forms data group will refer to a specific kind of data with relation to a consumer. For example, all of the consumer's past addresses are a forms data group.

A "forms data field" will refer to a specific item of data with relation to the consumer. For example, the consumer's address will be one forms field. The consumer's previous addresses will each be another forms data field. Therefore, a forms data group can include more than one forms data field, and, in this case, the forms data group of the consumer's previous addresses, includes multiple forms data fields, each of which is a previous address. In most embodiments of the invention, each forms data field will be part of a forms data group, even if it is the only forms data field in that forms data group. For example, an individual's Online Profile will include only one forms data field in the forms data group "social security number", because an individual consumer only has one social security number.

In many embodiments of the invention, the form data group that each forms data field belongs to, can be determined by the spot that the consumer places this forms data field in, on the initial form. If some of the consumer's forms data is imported into the consumer's profile from other files, then the same methods described elsewhere in the application (Including, but not limited to, Optical Character Recognition, or OCR) to determine the location and nature of the forms data values (15) on forms can be used to determine the content of the forms data fields in those other files. Then these forms data fields can be imported, and, using prearranged sorting criteria, placed in appropriate forms data groups in the forms data storage (9) for the Online Profile of the consumer.

A merchant can designate the forms data field(s) or forms data group that goes into each place (Each form data value) on the merchant's forms. To give one example, a consumer will have the name "William Smith", and a merchant's forms will have a form data value which is the box for the consumer's name. The forms data field "William Smith" will be placed in the form data value of "name" when William Smith uses the invention to fill out a form. Some potential method in which this may happen include that the form field is "mapped", or alternatively tagged, or slotted, into the appropriate forms data value (15).

A transaction is an event that begins with the sending of a merchant's request for a consumer's forms data to the request service, in merchant-initiated transactions, and the sending of a request for release of the consumer's forms data to the merchant, in consumer-initiated transactions. A transaction ends with the receiving of the requested form and data by the merchant, (Or the incorporation of the requested forms data into a form in embodiments of the invention that are able to incorporate the requested forms data into a form) and includes the events between that any component of the invention participates in, between the beginning and ending of the transaction. A transaction is started, and a transaction ID is created (and an external transaction identifier is also created in embodiments of the invention that use an external transaction identifier) when the merchant or consumer sends the request to start the transaction to the request service.

Forms Data

"Forms data" refers to data that a consumer may need to place in forms. Forms data may be stored in a consumer's Online Profile (OP) and used to fill out forms. Forms data may include, but not be limited to, the consumer's name, birth date, phone number(s), email addresses, address, previous addresses, social security number, ethnicity, current and previous places of work, monthly income, health conditions, treating physician(s), previous medical history, the names of bank and brokerage accounts, and information about credit accounts, a copy of the consumer's credit report, information about the VIN number, make, model, and year of the vehicles owned or previously owned by the consumer, websites controlled by the consumer, and information about the consumer's vehicle insurance and other insurances. Forms data may also include the consumer's estimated monthly income, the list of any credit card accounts held by the consumer, the names of the consumer's spouse and children, the consumer's present and previous schools attended, the consumer's "next-of-kin", the addresses of the consumer's profiles on Linkedin.com, Facebook.com, Instagram, and other prominent websites, a list of the consumer's previous publications, a list of clubs to which the consumer belongs, the list of permits and improvements related to a property that the consumer owns, and virtually any other type of information. The initial form filled out by the consumer, when establishing an Online Profile (OP), will be expanded in the future to include additional sections, so that the consumer has the ability to include more types of forms data in the Online Profile as consumers' needs and merchants' needs change. Because the initial form can be "updated" via the internet, the initial form can be "updated" to include new, additional, sections, for both consumers newly accessing the invention and consumers who have previously utilized the invention. Consumers who have previously utilized the invention will therefore be able to add the information requested by these new sections of the initial from to the initial form. In some embodiments of the invention, the consumer will also be able to include other documents, such as birth certificates, marriage licenses, wills, living trusts, and trust deeds, and the consumer will also be able to include video files, and save them in the Online Profile (OP). This will allow a consumer to create a complete digital profile of his or her life and history.

In some embodiments of the invention, it will be possible to group several individual consumers' Online Profiles together to create a "family-accessible" Online Profile. In some of these embodiments, members of the family will have automatic, continuous access to certain tiers of each others' profiles. This will allow them to be continually updated regarding changes in certain parts of each others' forms data, such as changes in addresses. It will also be possible to create a "family" Online Profile that is controlled by one person. Copies of important documents such as wills and life insurance policies can be scanned and stored on this family-accessible profile or family profile. This will enable the "next generation" of a family to smoothly make use of these documents in the event that a member of the family dies or becomes incapacitated. The documents will be easily available to them on the family-accessible profile or family profile. This will also help to eliminate problems related to disputes over whether a will was forged, or which version of a will is the latest version. In some embodiments, every upload to a profile will be time-stamped. Therefore, a decedent's heirs will be able to refer back to the timestamp on the will that has been uploaded to a family profile, to determine when the will was executed. In the past, documents of this type (Including documents such as the location of bank accounts) were stored in paper copies. They might become lost or inaccessible over time, and in many cases, these documents were not all in one place. There was also sometimes controversy about which will was executed later, in cases where a testator has executed more than one will. The present invention eliminates theses problems.

In some embodiments of the invention, corporations and businesses may also have versions of an Online Profile where important documents such as articles of incorporation, private placement memoranda, monthly financial statements, and important contracts are stored. These documents can then be made accessible to individuals and other businesses as needed.

When an Online Profile does not belong to an individual, but to a group such as a family or a corporation, the individuals who have the right to alter or add to the data in the Online Profile will have to authenticate themselves, before so doing. Such authentication will be of the same form as the authentication that an individual would have to complete in order to alter or amend his own Online Profile.

A forms data field is "responsive" to a forms data value (15) when that forms data field contains the type of information that the forms data field ask; For example, the forms data field of the consumer's social security number will be responsive to the forms data value (15) of "social security number", and each of a consumer's past addresses will be responsible to a forms data value of "past address".

The Online Profile

An "Online Profile" (4) refers to a computer-readable data source where a user's information, including the information which the user, when acting as a consumer, might find to be useful, when filling out different kinds of forms, is stored. This information may be grouped into tiers (5). Online Profiles should usually be stored on remote servers or central programs or other locations securely accessible to the internet, and securely accessible to mobile devices connected to the internet. In a version of the invention where the software components are spread out among several different applications, the Online Profile will generally be stored in a location where it is accessible to the internet. A consumer's Online Profile (4) is a secure repository of the forms data, and transaction data, for that consumer. Other configurations of storage for the online profile are part of the prior art, and are explicitly part of the invention.

To achieve maximum benefit from the invention, the consumer's Online Profile should also include the information necessary for the consumer to act as a merchant, such as a method by which the consumer can receive forms data from other users. For example, the Online Profile (4) may include an email address for the consumer, to which completed forms can be emailed. In some embodiments of the invention, the consumer's Online Profile will also include a pre-loaded forms database (20), which will include a group of forms for which the consumer can act as a merchant, and can ask other consumers to fill out the forms, after which the consumer (now acting as a merchant) will receive copies of the completed forms. The Online Profile (4) might also include an instruction for completed forms to be delivered directly to the merchant interface of the consumer. The Online Profile, in most embodiments should include a capability for a "forms delivery preference", which is a preferred method of how the user wishes to receive completed forms. In some embodiments of the invention, the consumer will be able to change the form delivery preference using the consumer program (2).

Each type of form in the pre-loaded forms database (20) will have either a Form ID Code (11) or a Barcode matrix form ID Code (12), or both. This is to identify each type of form. The consumer will have the ability to upload the forms into the pre-loaded forms database (20) ahead of time, so that these forms are available when the consumer desires to act as a merchant.

The inventors would like to make clear that a user of the invention is not required to act as a merchant, and is not required to upload any forms into the pre-loaded forms database (20) or onsite forms database (22). A user can choose to engage only in transactions where the user is a consumer, or only in transactions where the user is a merchant. However, the invention contains the capability for the same user to act as a consumer or merchant in different transactions.

A user's Online Profile in most embodiments of the invention will therefore include a forms data storage, which contains tiers, that contain the user's forms data. The Online Profile will also include a transaction data storage, containing the transaction ID of every transaction where the user (acting as a consumer) filled out a form using the invention, and the Online Profile may include a pre-loaded forms database (20) and a forms delivery preference, which will specify how the user wants forms completed by other users (who are acting as consumers) to be delivered to the user. For example, the user could use the form delivery preference to specify that she wants completed copies of forms to be delivered directly to her copy of the merchant interface (18).

The user's Online Profile also includes the initial form in most embodiments of the invention. The user will start the Online Profile by accessing the invention and beginning to fill out the initial form. The user may be able to access the invention by using the consumer program, which will grant the user access to the initial form. Once the user has accessed the initial form, this will cause creation of a new Online Profile in most embodiments. The user may need to authenticate himself in order for the new Online Profile to be created, in some embodiments. In some embodiments of the invention, the user may be able to access the initial form by accessing a different component of the invention, such as the forms signer, request service, notification service, or central program, and the initial form will be stored in one of these components and connected to the Online Profile.

In some embodiments of the invention, each consumer using the system will have an "Iforms username", similar to the way that many individuals have "Apple IDs" or email addresses now. In theory, the "Iforms username" could be the same thing as an individual's username, phone number, or Apple ID.

The Consumer Program

In the first embodiment, and many other embodiments, of the invention, the consumer program (2) and merchant interface (18) will be different parts of the same "app" or program, so that the consumer can conveniently download both the consumer program (2) and merchant interface (18) at once.

In some embodiments, the consumer program (2) will have a "transaction manager" feature that communicates with the notification service, each time a stage in a transaction between a consumer and a merchant is complete, so that the consumer program (2) will inform the consumer each time a stage in a transaction between a consumer and a merchant is complete. The notification service will send this information to the consumer program, which will inform the consumer. This can be done via text messages, or via a "push" notification, in the same manner that many apps used on cellular phones presently send notifications to users when an event happens. This can also be done in other ways, however the inventors believe that "push" notifications and text messages will be the most convenient methods. This methodology can also create a trail of references that can be audited if desired.

The consumer program (2) will also have a "permission" feature that communicates with the request service, and has the ability to utilize the camera capability of a cellular phone, or other consumer device, to scan matrix barcodes or other scannable QR codes and send the data stream to the request service, The scan is converted to a string of text, containing a URL or identification code for the form, and then sent to the request service. This can be done with matrix barcodes, QR codes, and other visual codes. This means of sending information about the code to the request service will be used in most embodiments of the invention, including the first embodiment. The notification preference selector will allow a consumer or merchant to select the steps in a transaction, for which the consumer or merchant desires to be given notifications concerning the completion of the steps. The notification preference selector is intended to be a feature of both the consumer program (2) and merchant interface (18). A consumer and merchant involved in the same transaction could theoretically select different notification preferences, so that one party receives notifications of some steps of a transaction, of which the other party has declined to receive notice.

Most embodiments of the consumer program (2) will also include a "final check" feature. This will display a list of the information to be released to the merchant, after the consumer has authenticated himself or herself and the forms data fields in the relevant tiers are retrieved. Next to each forms data field will be a box which can be checked or unchecked, or another item which indicates whether the consumer desires to release that specific form data field to the merchant. If the box is checked, this gives consent for the consumer to release the specific forms data field next to the box, to the merchant. The default condition will be for the boxes to all be checked, but a consumer can manually "uncheck" some or all of the boxes, and prevent specific forms data fields from being released to the merchant.

In some embodiments, therefore, the consumer program will include a transaction management feature, notification preference selector, a permission feature, a list of the kinds of information included in each tier of the forms data storage, a notification feature, a "final check" feature, and a "Forms Data Updates" feature that will allow the consumer to access his or her Online Profile, authenticate himself or herself, and change or add to the forms data in the Online Profile.

The Merchant Interface

The merchant interface (18) is the interface through which the merchant will interact with other software components, including the transaction signer (which may be stored on the central server (16) or central program (21) or another location) to acquire some or all of the consumer's forms data. In some embodiments, the merchant interface may also include the on-site forms database (22), which will not be stored remotely but will be stored on the merchant's computer system. In the on-site forms database (22), the user (here acting as a merchant) can store forms, into which consumers' forms data can be imported. In other embodiments of the invention, there will be a pre-loaded forms database (20), which will be part of the merchant's Online Profile. Still other embodiments of the invention will include neither the on-site forms database or the pre-loaded forms database. The merchant interface (18) will also have a "gateway" feature, by which the merchant interface will receive QR codes, matrix barcodes, or other codes that are sent to the merchant interface by the notification service, and then the merchant interface will display these codes so that consumers can take pictures of these codes as part of the process of releasing their forms data to the merchant.

In some embodiments, the consumer's forms data will be imported into a form stored on the merchant's computer system. Alternatively, the consumer's forms data may be delivered to the merchant in the following manner: The merchant interface will send a request for the desired forms data to a merchant API (Application Programming Interface), which is a part of the transaction signer. Then, the merchant API will return the desired forms data to the merchant interface. The merchant, using another application, will have pre-designated the forms data fields (Or the forms data group) that goes into each forms data value on the merchant's form. In other words, the merchant will have pre-designated that the first name of the consumer goes into a forms data value labeled "first name", the last name of the consumer goes into a forms data value labeled "last name", etc. The merchant interface will "hand off" the forms data fields to the other application, by transferring the forms data fields to the other application. This will place the appropriate forms data field in each forms data value on the merchant's form.

In other embodiments, the merchant interface will send a request for the desired forms data to a merchant API, which is a part of the transaction signer. Then, the merchant API will return the desired forms data to the merchant interface. The merchant interface will display the acquired forms data fields, and the merchant will integrate these forms data fields into its forms, or CRM system, using whatever method the merchant desires.

In still other embodiments of the invention, the merchant's CRM (Customer Relations Management) software will connect directly to the merchant API, which will send the desired forms data fields to the CRM system. Then, the CRM system will integrate this information into the merchant's desired form.

In some embodiments, the merchant interface (18) will have a "transaction manager" feature that receives information from the notification service, each time a stage in a transaction between a consumer and a merchant is complete, so that the merchant interface (18) will inform the merchant each time a stage in a transaction between a consumer and a merchant is complete.

In some embodiments, copies of completed forms, which include data that the merchant has requested from consumers, will be delivered to a "Finished forms" feature of the merchant interface, where the completed forms will be saved, either by being saved in a file, or through another manner. From the Finished forms feature, the completed forms can be electronically copied to other programs, or printed out.

Some embodiments of the merchant interface will therefore include, but not be limited to, a notification preference selector, a transaction manager feature, a Finished forms feature, an on-site forms database, and a gateway feature, and a list of the types of forms data included in each tier, and a "Forms Data Updates" feature that will allow the merchant to access his or her Online Profile, authenticate himself or herself, and change or add to the forms data in the Online Profile.

In one embodiment of the invention, when the merchant decides to initiate a transaction, the merchant will use the merchant interface to send a notification to the request service. The notification will include the kind of form that the merchant desires to be completed, in some embodiments. For example, the notification may include the name for the form "Form-001" for the merchant "John Doe". The notification might also include the Form ID Code (11) or Barcode Matrix Form ID code (12) of the desired form. The request service will then generate a unique QR code, or another code such as a matrix barcode or regular barcode, and send this unique code to the merchant interface. This will be the consumer response code (24). The consumer response code (24) may include information that codes for the Form ID Code (11) or Barcode Matrix Form ID Code (12), and the consumer response code (24) may also, include information which codes for the Transaction ID, or External transaction identifier Code, in some embodiments. Therefore, in some embodiments, the consumer response code (24) will include information drat codes for both the Form ID Code (11) and the Transaction ID. The request service will also create the transaction listener and inform the transaction listener of this consumer response code (24), so that the transaction listener will be able to recognize the consumer response code (24), or a data stream that codes for the consumer response code, when it is sent by the consumer. The merchant interface will receive the consumer response code (24), and be able to display the consumer response code (24) on a screen, or print out the code. The consumer response code, in most embodiments, will include information about the specific type of form that the merchant intends for the consumer to populate with his or her forms data. As an example, if a merchant is a rental company, and the form is the rental company's lease application for a specific building, the code will contain information that indicates that the merchant wishes for the consumer to fill out the lease application for that specific building, as part of this transaction. This information can include the form ID code or Barcode matrix form ID code of the lease application for that building.

The consumer program (2) will include the permission feature, which will scan the consumer response code (24) generated by the merchant interface of the merchant, and the information in the consumer response code (24) will be sent by the consumer program (2) to the remote server where the transaction listener will recognize the consumer response code (24) as belonging to a specific transaction. In most embodiments of the invention, the consumer program (2) will not save the picture on the consumer device, but will convert the scanned consumer response code (24) to a stream of text, and send this stream of text to the transaction listener, as discussed above. The stream of text, in most embodiments, will include information about the specific type of form that the consumer intends to populate with his or her forms data. As an example, if a merchant is a rental company, and the form is the rental company's lease application for a specific building, the stream of text will contain information that indicates that the consumer wishes to fill out the lease application for that building. After the consumer has authenticated himself in any other way required, the transaction listener will then transmit to the notification service and forms signer that the consumer has accepted the transaction. In most embodiments, the transaction listener will also inform the notification service and forms signer that the consumer has requested a resource, i.e., a form to be populated.

The QR Code, or other type of code, that is the consumer response code (24) generated by the request service, can also be sent, in some embodiments, from the merchant to the consumer electronically, by a text message, email, an "in-app" message, a push notification, an "alert", as that term is used with reference to mobile devices, or a pull notification, or in another way. The consumer can then use the permission feature of the consumer program (2) to transmit the consumer response code (24) to the transaction listener (3).

In other embodiments, the request service will inform the forms signer that the merchant has requested that a transaction be initiated, and the forms signer will create the consumer response code (24). Then, if the consumer sends the consumer response code to the transaction listener, the transaction listener will confirm with the forms signer that the consumer has sent the correct consumer response code (24) to indicate a desire to start a transaction. The transaction will only be started if the consumer has sent the correct consumer response code (24).

More Information about Central Software Components

The Online Profiles of users, the request service, the forms signer, the notification service, and any transaction listener are stored in locations where they are capable of electronically communicating with each other, and electronically communicating remotely from the consumers and merchants who are using the invention.

As non-exclusive examples, the Online Profiles of users, the request service, the forms signer, the notification service, and any transaction listener may be stored on a central server. Alternatively, they may be stored as part of a single, central program. The Online Profiles of users, the request service, the forms signer, the notification service, and any transaction listener may be stored as parts of separate programs in communication with each other, or stored by any other method that is part of the prior art.

The Central Server

The central server is the server (a form of computer hardware or virtual machine) where the Online Profile (4) and Tiers (5) and forms data storage (9) are located in the first embodiment of the invention. It will be understood that a cluster of servers can theoretically fulfill the functions of the central server. The central server might also theoretically include another form of computer hardware or software besides a server, as long as the computer hardware or software designated as the central server can perform the tasks required of the central server.

In some embodiments of the invention, the organizational scheme of the software components is important, because this organizational scheme reduces the number of processing steps, so that the merchant can receive the completed form more quickly. This will allow merchants to receive forms related to a larger number of consumers simultaneously, and process the forms faster.

The Central Program

The central program (21) is a program in some embodiments of the invention that contains the request service, form signer, and notification service, where these components are all subcomponents of one program. In a second group of embodiments of the invention, these components are all related because they are subcomponents of one program, the central program, (21) but these three components do not need to be stored on the same server or related servers. In a third group of embodiments of the invention, these three components are parts of different applications that interact with each other over a virtual private network. In this third group, there is no central program.

The Transaction Listener, Forms Signer, Request Service, and Notification Service The transaction listener (3) is a software component that is created when a merchant sends the request service a request for some of the forms data that a consumer has stored in his Online Profile. The Central Server (16) or Central Program (21) may receive this request in embodiments that use the Central Server (16) or Central Program (21), respectively. In most embodiments, the transaction listener (3) is an API endpoint. The transaction ID (6) refers to the unique ID assigned by the invention to each transaction. The invention will use the most advanced methods presently available in the art to assign transaction IDs in a manner that makes each transaction ID unique.

The forms signer (7) is the software component that acquires forms data from the tiers (3) in the Online Profile (4). In a transaction, the forms signer will query the relevant tiers of the Online Profile, which the consumer has given permission to search, for the information that the merchant has requested. The forms signer authenticates this data, and sends a consumer's forms data to the merchant after the merchant requests the forms data. In most embodiments of the invention, the forms signer will complete forms for consumers by importing the relevant forms data from a consumer's Online Profile into the desired form from the merchant's pre-loaded forms database (20), and then sending the completed form to the merchant.

The forms signer, in most embodiments of the invention, will also ensure that this information is accurate by using historical transaction data to verify the accuracy of the forms data that has been delivered. For example, the forms signer will store a hashtag or another type of metadata tag signature, or digital signature, when the forms signer sends the forms data to the merchant. The hashtag will describe the forms data that has been transmitted. This can be used later to verify the exact nature of the forms data that was sent to the merchant at the time of the transaction. This hashtag will be stored in the transaction data storage (10). This can be used as a transaction receipt.

The request service (17) is a software component that receives information from a merchant, and creates the transaction listener and transaction ID. The transaction data storage (10) is a memory where the transaction IDs of all the transactions where this specific consumer's forms data have been sent to any merchant. In some embodiments of the invention, the identity of the "tiers" of information sent to that merchant will also be recorded in the transaction data storage (10). The information about the tiers can also be included in the hashtag recording information about the transaction, and stored in the transaction data storage by the forms signer, in embodiments of the invention that use this specific type of hashtag. Other methods of including a record of past transactions in the transaction data storage are also included within the scope of the present invention.

The transaction data storage (10) is exceptionally useful because a consumer can use the transaction data storage (10) to keep track of the identity of the merchants who have received the consumer's forms data via the invention, and also to keep track of the types of forms data that these merchants have received.

The forms data storage (9) is the software component of the invention that contains the "forms data", the data that the consumer may use to fill out forms. The forms data within the forms data storage of the first embodiment of the invention is divided into tiers.

The notification service (8) is a software component of the invention that provides optional notifications to the consumer and the merchant. These notifications can be sent throughout the process of a consumer giving the merchant permission to access the consumer's forms data, and the merchant accessing and receiving the forms data. These notifications may be sent by text message, email, "push notification", an "alert", or any other form through which notifications may be given. Many games presently used on camera phones inform the user when an event happens in the game, by making something similar to a small text message on the phone or other computing device. This is called a "push notification". The present invention's consumer interface will have the same capability. Push notifications can be used for the notification of the completion of each stage of the process, so that the consumer and the merchant will be aware that this particular stage of the process has been completed.

The notification service can be designed to send notices to the consumer and merchant of completion of a larger number of the operations that happen within each stage of the process of a) the consumer giving the merchant permission to access the consumer's forms data, and b) the merchant accessing and receiving the forms data. This will cause the consumer and merchant to receive more notices during each transaction. A version of the invention with the notification service designed in this way is explicitly within the scope of the invention. However, most consumers and merchants will probably not desire a version of the notification service that sends too many notifications, therefore a version of the invention that send notification of completion of only some stages of the process is likely to be used.

Therefore, the notification service also includes the ability for either the consumer or merchant to change his or her "preferences" within the notification service, so that the notification service does not send a party notifications of the completion of a stage, when that party does not want notification of completion of that stage. This will be accomplished by a notification preference selector, which will be part of both the consumer program (2) and merchant interface (18).

Definitions of ID Codes

The Form ID Code (11) and Barcode Matrix Form ID Code (12) represent specific codes that identify specific forms that the Merchant may have previously uploaded into the invention, in particular the pre-loaded forms database (20) or the on-site database (22). The Barcode Matrix Form ID Code would be a matrix barcode, and the Form ID Code would be another kind of code. A form may have a Form ID Code, a Barcode Matrix Form ID Code, or both, depending on which embodiment of the invention is being used. The merchant would generally also have previously identified the type of data that is placed on each part of the pre-loaded form. These previously uploaded forms can be completed more quickly by the invention than regular forms, though some embodiments of the invention are also capable of completing regular forms that have not been pre-loaded.

The external transaction identifier code (19) is a code in some embodiments of the invention that the invention can give to the consumer if the consumer starts completing a form using the system but then must finish the form later. The consumer can type in, or otherwise enter, the transactional external identifier code, in a consumer device, after authenticating himself, to get back to his uncompleted form. In most embodiments of the invention, this will not need to be the same consumer device that the consumer used to start the transaction. The external transaction identifier code can be different from the transaction ID, but does not have to be different. The purpose of this difference is to make the system more secure, and makes "hacking" more difficult. A party in possession of the transaction ID might be able to access and manipulate the internal processes of the request service, form signer, and notification service. If the external transaction identifier code is different from the transaction ID, this will reduce the chances of such manipulation, because the transaction ID will not be broadcast to the consumer, and therefore, it will not be known to any human being. All software components of the invention will be designed with security features to prevent unauthorized parties from manipulating their internal processes, but the difference between the transaction ID and external transaction identifier code will help with this protection. The inventors expect that the invention will securely protect consumers' and merchants' forms data and other data, even in embodiments of the invention that do not include an external transaction identifier code, and embodiments that use only the transaction ID to identify a transaction both internally and externally.

The consumer response code (24) is a code that the consumer can send to the request service in some embodiments of the invention, or to the transaction listener in others, to designate that the consumer wishes to engage in a transaction. The consumer response code (24) can be a matrix barcode, QR code, or another kind of code. In merchant-initiated transactions, the consumer response code (24) will be sent to the transaction listener.

Forms of ID Codes

Several components of the invention, such as the Form ID code (11) and Barcode Matrix form ID code (12) are identification codes that designate specific components of the invention or other specific items. For example, the Form ID code (11) and Barcode Matrix form ID code (12) refer to unique identifiers given to types of forms. The components of the invention that are identification codes may be alphanumeric codes, bar codes, matrix bar codes, QR codes, or any other type of codes known to exist in the prior art, that would fulfill the purposes of the invention (except in cases where a code component is designated to have a specific form, such as the Barcode Matrix form ID code (12)). For example, the Form ID code (11) can be an alphanumeric code, or QR code, or one of other types of codes known in the prior art.

Both a Form ID Code and a Barcode Matrix Form ID Code can include information about the forms data values (15) in forms that they respectively represent.

Storing the Data within the Consumer's Online Profile

When a consumer first establishes a Online Profile (4) with the invention, that consumer will enter some or all of his forms data into the tiers (5) within the forms data storage (9) of his or her Online Profile (4). The forms data entered into the forms data storage (9) by the consumer will be the forms data that the invention can later access to send to merchants. This forms data will be encrypted using industry-standard encryption or a stronger method of encryption.

The consumer will establish an Online Profile by authenticating himself or herself. The consumer may authenticate himself or herself by confirming an email address, and also offering information such as a birth date and the address, name, and credit card number associated with a credit card (The same information that the consumer would need to offer, when making a credit card purchase online). The credit card company associated with the card will confirm the address associated with the card, which is a form of identification to the consumer. The invention may also ask for other personal information about the consumer, so that the consumer's identity can be confirmed. For example, the invention may also ask for the consumer's fingerprint to be scanned, so that it can be compared with copies of the consumer's fingerprint in any known databases. The invention may also ask for a picture, so that this picture can be compared to any available pictures of the consumer, including the picture on the consumer's "Facebook" profile. After the consumer has authenticated himself or herself, the invention may also ask for a recording of the consumer's voice. This recording can then be later used to authenticate the consumer's identity when the consumer asks for information to be released to a merchant, or when the consumer wants to update his or her forms data. Later on, when the consumer wants information to be released to a merchant, or wants to update or add to his or her forms data, the invention may ask for the consumer to speak, so that the consumer's voice can be compared with the voice that the invention has recorded.

In the first embodiment of the invention, the consumer will fill out one online form, when he or she establishes an Online Profile within the invention, after authenticating himself or herself. When the consumer's identity is confirmed, the consumer's Online Profile will be established.

This online form will include forms data values where a consumer can enter forms data fields concerning a large number of categories of information. The sections in the online form will be "expandable" so that if the consumer needs to input a large number of forms data fields in one category of forms data values, the section of the online form that includes this section of forms data values will expand to accommodate the additional forms data fields. For example, if the consumer has a large number of past addresses, the part of the one online form entitled "past addresses" will expand to accommodate all these past addresses.

The consumer can choose not to input all of the information that the form requests. The invention will still function if the consumer chooses this. For example, some consumers may choose not to include their health information in the form. Any information that the consumer does not input into the form will not be available to be shared with merchants later. The invention will, however, save the information that the consumer does input into the form. This information may be saved in the tiers. The consumer will then be able to share any information that the consumer inputs into the form, with merchants.

The form will request forms data fields including, but not limited to, the consumer's name, previous addresses, phone number, previous phone numbers, social security number, and other information, medical history, financial account numbers, and the institutions where these accounts are held, and also the consumer's arrest history, criminal history, and other information. In most embodiments of the invention, the consumer can choose not to answer some of the questions in the form if the answer simply does not exist. For example, a consumer who has never been arrested would not need to answer questions about the consumer's arrest history, and would leave that part of the form blank. Other kinds of information can also be among the kinds of information requested by this form, in other embodiments of the invention, for example, the form can theoretically include the internet address of the consumer's Facebook profile. These other embodiments are also within the scope of the current invention, and if the form requests additional kinds of information, this will not substantially change the functioning of the invention.

In addition, this one initial form may be expanded, in the future, to give the consumer the opportunity to include additional information. The initial forms data that has been placed into the form will remain intact, but there will also be places for additional types of form data. For example, the initial form may in the future be expanded to include the consumer's "username" on a program which does not now exist but has become popular at that point (As Facebook and Instagram once did not exist but are now very popular). The consumer can then authenticate himself again and add this additional forms data, to his Online Profile, if the consumer so chooses.

In some embodiments of the invention, the consumer may input his or her forms data into the invention through another method besides filling out a form, but filling an online form will be the most convenient method, of entering his or her forms data, in most embodiments of the invention. In some embodiments of the invention, other files may be uploaded by the consumer, such as video files and files such as copies of wills and life insurance policies.

The consumer can also return to the form later, and add more information, after authenticating himself or herself again. The consumer can also change the information that he or she has already placed in his or her Online Profile. The main method through which consumers will input their data into an Online Profile will probably be through typing it into the Online Profile. However, consumers could also "scan" the information into the Online Profile through a PDF form, in some embodiments, or could "import" the data from another source, such as another website. Consumers could also "scan" the information into their Online Profiles by importing digitized documents, allowing forms data written on these documents to be captured by "OCR", or Optical Character Recognition. Some embodiments of the invention will permit the consumer to upload files such as video files and copies of life insurance documents. Consumers could also theoretically input some types of forms data into their Online Profiles through speaking the information into an electronic device capable of receiving input through audio.

Other methods of inputting the consumer's forms data into the consumer's Online Profile, including all methods of inputting the consumer's forms data that are known in the prior art, are also explicitly included in the invention. In some embodiments of the invention, the forms data group of each forms data field that the consumer inputs into the form will be identified immediately by the invention so that the forms data group that each forms data field belongs to is clear immediately. The identifier designating the forms data group may be an alphanumeric code, matrix barcode, or something else.

In the first embodiment of the invention, the information that the consumer places in the form may be grouped into tiers (5), which will be part of the forms data storage within the user's Online Profile (4). The initial form will be connected directly to the tiers in the forms data storage (9), and the forms data which is placed in the initial form will be sent to the forms data storage (9), where this forms data will be separated into tiers (5) according to pre-programmed sorting criteria that will thematically determine the type of information that goes into each tier. These pre-programmed sorting criteria might be part of the forms data storage, or part of the initial form. These sorting criteria will place similar information together, for example, information about the consumer's past addresses will be placed in the same tier.

The initial form will be part of the forms data storage, but will be accessible via the consumer program (2), in some embodiments of the invention. The consumer will need to authenticate himself or herself to access the initial form, after the consumer has started an Online Profile. This authentication may include, but is not limited to, voice-based encryption, password, based encryption, identification of a consumer device's "IP address" or Internet Protocol address, and other methods.

In other embodiments of the invention, the initial form, will be separate from the forms data storage, but will be part of the Online Profile. The consumer will create an Online Profile by accessing the invention, possibly through a website, and will authenticate himself or herself, after which the consumer will be taken to his or her newly created Online Profile, and will fill out the initial form.

In some embodiments of the invention, the consumer might access the initial form by accessing the central program, and then being taken to the initial form. In some of these embodiments, the initial form can be separate from the forms data storage, and can be accessed via the central program, so that the consumer creates the Online Profile after accessing the initial form.

The initial form can also be placed within other locations in the invention, and these are also explicitly part of the claimed invention.

In the first embodiment, the types of data that will be included in each tier will be predetermined. For example, the tier that previous addresses will be placed into will be predetermined, the tier that previous email addresses will be placed into will be predetermined, the tier that medical information will go into will be predetermined, and the tier that information about brokerage and bank accounts will go into will be predetermined. The tiers in the first embodiment will be organized thematically, for example, medical information will go into one tier, and information about the consumer's past addresses will go into a different tier. For example, "tier 5" may be medical history information, and "tier 4" may be bank account information. Another method of organizing the tiers is possible, but will probably be less efficient.

The inventors wish to make clear that the theme of each tier, the number of tiers, and the type of information that goes into each tier are not limited by any technological constraints inherent to the invention. In other words, a person building an example of the invention may select any theme that he wishes for each tier, may include any number of tiers, and may decide to include any type of information that he wishes in each tier.

The consumer will also have to provide information allowing the invention to contact the consumer when a merchant requests the consumer's form data. For example, the consumer may have to provide his or her phone number and email address, so that the consumer can be contacted by phone number or email address, respectively, or sent an alert or "push" notification, so that the consumer can give the merchant permission to receive the consumer's forms data. The consumer should provide his or her phone number, or other information sufficient to be able to receive text messages or "push" notifications, at different stages of the process when the consumer's forms data is sent to a merchant. The invention can transmit a notification to the consumer, informing the consumer that the merchant is seeking the consumer's forms data.

The consumer will have the option to add to, or change, the consumer's forms data at a later point in time, after authenticating himself or herself again. For example, if the consumer changes his or her phone number, the consumer will be able to update his or her phone number that is listed in the forms data storage. Access to the consumer's Online Profile will be protected by encryption, to ensure that only the consumer may change his or her forms data. Encryption that is standard in the industry, or stronger, will be used.

Encryption and Protecting the Parties' Information

Two-factor authentication involves granting a person access if he has verified his identity, and verifying that person's identity with two or more different forms of identification. For example, the present invention might use two-factor authentication by requiring a user to speak and comparing this to a recording of the consumer's voice (thus making the user's voice one form of identification) and requiring the user to input a secret code (The second form of identification) before the user is granted access to the website. Two-factor identification is generally considered more secure than identification based on one form of identification, such as voice alone. It is also possible to use three-factor identification, four-factor identification, and other forms of "multi-factor" identification using more factors.

In many embodiments of the invention, the consumer's Online Profile will require a consumer to verify their identity using two-factor, or other multi-factor identification, before the consumer is allowed to modify or add to the forms data saved on the consumer's profile. A consumer will also need to verify his or her identity using two-factor, or other multi-factor identification, when the consumer authorizes a merchant to access the user's forms data.

Some factors that can potentially be used by a consumer to authenticate his or her identity include codes that must be entered by the consumer, identification of the consumer's voice, detection of the consumer's device ID (Such as the Universally Unique Identifier, or UUID, used by cellular phones), detection of the consumer's IP address, and detection of the consumer's thumbprint via the consumer scanning his or her thumb on the screen of the consumer device (2). Other industry standard methods can be used to authenticate the consumer's identity.

A merchant will need to authenticate itself, in order to start an Online Profile. After the merchant has authenticated itself, the merchant's Online Profile will be started. Merchants will also use industry standard methods to authenticate themselves and prove their identity, so that they may access a consumer's information. Some methods of authentication for the merchant include the authentication methods listed above, and other industry standard authentication methods.

After the merchant authenticates itself, it can either upload forms to a pre-loaded forms database (20) that is part of the merchant's Online Profile, or upload forms to an on-site forms database (22) that is part of the merchant interface (18), or upload only information about the forms data values (15) or forms data groups, or form data fields, required to fill out each form to the pre-loaded forms database (20), or upload only information about the forms data values (15) or forms data groups, or form data fields, required to fill out each form to the on-site forms database (22). For example, the merchant may upload information to the pre-loaded forms database (20) about a specific form, saying that the form contains the forms data values "name", "phone number", and "address", without uploading the form itself to the pre-loaded forms database (20).

The merchant can also engage in a combination of these; For example, the merchant may decide to upload some forms to a pre-loaded forms database (20), and upload information about the forms data values (15) or forms data groups required to fill out other forms to the pre-loaded forms database (20). The merchant can also decline to upload forms, and can access consumers' forms data, that is released to the merchant, via API directly to the merchant's applications.

The forms signer will be unable to deliver completed versions of the desired form to the merchant in a scenario where the merchant does not upload a form to the on-site forms database (22) or pre-loaded forms database (20), but instead uploads nothing to one of these databases, and uploads to the other database a list of the forms data values (15) or forms data groups required to fill out the desired form. The forms signer will instead use a merchant API to return to the merchant the forms data fields that belong within the forms data groups, that the merchant has requested, or correspond to the forms data values (15) that the merchant has requested. The merchant can then integrate these forms data fields into a copy of the desired form using the merchant's CRM system.

If a consumer starts a form, but does not complete it, then this uncompleted form can be saved in any of several locations. Depending on the embodiment of the invention, the uncompleted form can be saved in the transaction listener, the forms signer, the request service, the transaction data storage, the pre-loaded forms database (20), the on-site forms database (22) or another location.

Further Controls on the Level of Access to Consumers' Data

In some embodiments of the invention, the number of tiers of a consumer's forms data that a merchant will be able to access depends upon the number of forms of authentication that the merchant has provided of its own identity. For example, a merchant that provides only its name and address may only be able to access the lowest tiers of information and a merchant that verifies its phone number will be able to access higher tiers of information, and a merchant that provides voice-based identification will be able to access still higher tiers of information. This is not the only possible sequence of the types of access that a merchant may gain if the merchant provides more types of authentication. The thresholds for the tiers of information that a merchant may access, depending on the level of authentication that the merchant has provided, may be set in a variety of different ways, all of which are part of the present invention.

The merchant can start an Online Profile and provide one type of authentication, and return to the Online Profile later and provide other, additional types of authentication.

In most embodiments of the invention, the merchant will only need to provide this authentication when the merchant establishes an Online Profile, or returns to the Online Profile to provide a greater level of authentication. However, in some embodiments of the invention, the merchant will need to provide additional authentication during each transaction where the merchant wishes to acquire certain categories, or certain higher tiers, of a consumer's forms data.

One Possible Interaction of the Merchant Interface and the Form Signer

In the first embodiment of the invention, the merchant will use an industry standard web browser as the Merchant Interface, there will also be an "app" for mobile device access. The merchant will establish an Online Profile, in which the merchant will establish his or her identity by authenticating that identity. In one embodiment of the invention, the merchant will not have to pre-load any forms into the software components of the invention. In another embodiment of the invention, the merchant may also store pre-loaded forms in an on-site forms database (22) within the merchant's copy of the merchant interface (18). In still another embodiment of the invention, the merchant may also upload forms into a pre-loaded forms database (20) held online within the merchant's Online Profile.

In other embodiments of the invention, there will be a dedicated merchant interface that can be downloaded by the merchant, and can be downloaded along with the consumer app (2).

Pre-Loading Forms

In one embodiment of the invention, when a merchant pre-loads forms using the merchant interface, the merchant can save these pre-loaded forms in the pre-loaded forms database (20) or the on-site forms database (22). Each form type will be identified by a Form ID Code or Barcode Matrix Form ID Code. The merchant can select the form data fields that will be placed into each forms data value (15) on each of the merchant's forms, or select the forms data groups that these forms data fields will be drawn from. The identity of these forms data fields or forms data groups will then be saved with reference to that specific form type. Both the pre-loaded forms database (20) and the on-site forms database (22) will be capable of saving this information, and associating this information with the form type, which will be identified by a Form ID Code such as a Barcode, or Barcode Matrix Form ID Code.

In some embodiments, the tier that the forms data fields (or forms data group) that are responsive to each forms data value in a form is determined, and recorded, and saved in the pre-loaded forms database (20) along with the form, or along with the record of the forms data values in that form. The tier(s) that contain the forms data fields (or forms data group) that are responsive to each forms data value (15) in a form is recorded, and saved in the pre-loaded forms database along with the form, or along with the record of the forms data values in that form (depending on whether the form itself or record of the forms data values was saved). This is done via sorting criteria, which utilize the form data values (15) in the form, and also determine the forms data groups that are placed in each tier (5) of a user's Online Profile (4), to determine the tiers where the forms data fields responsive to each of the form data values (15) on the form will be found.

In some embodiments of the invention, when the forms signer receives the requested forms data from the forms data storage (9), the forms signer will scan the pre-loaded forms database for the form with the appropriate Form ID code (11), or Barcode Matrix form ID code (12) given by the merchant, and the forms signer will then match the forms data fields that the forms signer has received to the forms data field or forms data group responsive to each forms data value (15) on the form.

The measures listed in this section of the application will ensure that the correct data is transposed into each place on the merchant's forms, for example the name of the consumer will go into the "name" space, the "address" of the consumer will go into the "address" space, etc. Each type of form has a unique ID, such as a Form ID code (11), or Barcode Matrix form ID code (12). Therefore, when the merchant tries to acquire a consumer's forms data to fill out a form, the merchant can designate the Form ID code (11) or Barcode Matrix form ID code (12) of the form that the merchant wants to be filled out, and the form data field selections of the merchant with relation to the selected type of form will be applied to the individual form being filled out.

In most embodiments of the invention, the merchant will be able to use the merchant interface (18) to designate the form that the merchant wants the consumer to fill out, when the merchant uses the merchant interface (18) to contact the request service (7) to initiate a transaction. The consumer response code (24) that is sent from the request service to the merchant will then include information that is used to identify the form that the consumer should fill out.

In embodiments of the invention that do not include a merchant interface, other methods will be used. For example, the merchant may use another form of communication with the request service (7) to select a form from among the saved forms in the merchant's pre-loaded forms database (20). These forms will all have Form ID Codes (11), and/or Barcode Matrix Form ID Codes (12). The forms signer will be able to determine the forms data field or forms data group that should be entered into each forms data value (15) on the form (The forms data field or forms data group that is responsive to each forms data value (15) on the form).

The following will happen in most embodiments of the invention: For each space on the form (forms data value) (15), the forms signer will import the forms data fields from the consumer's Online Profile (4) that belong to the corresponding form data group to the form data group responsive to that particular forms data value (15), in the form, and the forms signer will place these forms data fields into that particular forms data value (15), on the form. The imported forms data fields responsive to each forms data value will be placed in that forms data value (15), completing all the forms data values (15) for which the consumer provided responsive forms data in his Online Profile (4), and also permission to release this responsive forms data in the transaction. Some or all of the forms data values on the form will therefore be completed. This completed form will then be delivered to the merchant. In some embodiments, the completed form will be delivered to the completed forms section of the merchant interface of the merchant.

In some embodiments, if the form that is to be filled out is not in the pre-loaded forms database (20), or the merchant is using a version of the invention that does not include a pre-loaded forms database (20), the forms signer will transmit the consumer's forms data fields to the merchant interface. The merchant interface will query the on-site forms database (22) for the appropriate form, by searching the on-site forms database (22) for the form with the correct ID (In some embodiments the correct ID will be the correct form ID code (11) and/or the correct barcode matrix form ID code (12)). The merchant interface will then fill out the form by importing the form data fields from the consumer's Online Profile (4) that belong to the forms data group that corresponds to the forms data group responsive to that particular forms data value in the form, and the merchant interface will place these form data fields in that particular forms data value on the form. This completed form will then be delivered to the merchant. In some embodiments, the completed form will be delivered to the completed forms section of the merchant interface of the merchant.

In another embodiment of the invention, mapping techniques will be used by the forms signer to discern the form data fields that are responsive to each form data value (15). For example, the form signer can be programmed to recognize the appropriate content for most forms data values (15). For example, the form signer can be programmed to recognize that that a forms data value (15) which contains the term "last name" is an appropriate place to place the forms data field for the last name of the consumer. Therefore, the forms signer can locate the desired form by the form's ID code ((11) or (12) in some embodiments), and then scan that form and recognize the type of information required by each forms data value. Then, the forms signer will match these types of information to the forms data fields that have been retrieved from the forms data storage, and place the forms data fields with that most closely match the information requested for each forms data value (15) in that forms data value (15). The forms signer will then send the completed form to the completed forms section of the merchant interface (18) of the merchant.

In some embodiments, if the form that is to be filled out is not in the pre-loaded forms database (20), or the merchant is using a version of the invention does not include a pre-loaded forms database (20), the forms signer will transmit the consumer's forms data fields, that the forms signer has retrieved, to the merchant interface. The merchant interface will query the on-site forms database (22) to determine if the form to be filled out is part of the on-site database. After the desired form is found, the merchant interface will then import the consumer's appropriate forms data fields into the form using the same techniques that would be used if the desired form had been found in the pre-loaded forms database.

In still another group of embodiments, the forms signer will scan the pre-loaded form that has been uploaded to the on-site forms database (22) that the consumer wants to fill out, and the forms signer will then determine the form data fields that belong in each form data value (15). In this embodiment of the invention, the forms signer will include a "data value identifier" that scans each type of information requested on the pre-loaded form, and determines the type of information that that is being asked for. For example, a box entitled "last name" will be asking for the consumer's last name. The forms signer will then select the appropriate forms data fields from the data that the forms signer has acquired from the tiers in the consumer's Online Profile, and map this information into the forms data values (15) on the merchant's form, and send the form to the merchant.

The merchant can then print out the completed form or store it electronically in the merchant's computer systems.

In a different embodiment of the invention, the forms signer will interact with the on-site forms database (22) and import the forms data fields that are required by the form into the desired form, in the onsite form database, in one of the manners discussed above.

Whenever forms are pre-loaded, they can be scanned using one of the standard computer programs that is capable of scanning one example could be PDF files, including, but not limited to, those programs created by Adobe. The forms can then be uploaded into the components of the invention where the forms are needed.

Some Embodiments without the Pre-Loaded Forms Database or On-Site Forms Database In still another group of embodiments, there will be no pre-loaded forms database or on-site forms database, but the merchant will have used the merchant interface to designate the forms data values and identity code (Form ID Code (11) or Barcode Matrix Form ID Code (12) in some embodiments) of the form. Then, when the merchant wishes to acquire a consumer's forms data, the merchant will send a request to the request service, indicating the identity code of the form desired, and the forms data groups from which forms data fields are desired. The merchant interface will ask the forms signer for the forms data groups, pertaining to the consumer, that pertain to the forms data values (15) of the desired form. The forms signer, after searching those tiers (5) in the forms data storage (9) to which the consumer has allowed access, for forms data fields that are part of the responsive forms data groups, will send any responsive forms data fields. These forms data fields will be sent to the merchant interface, or alternatively to a merchant API, from which the merchant can use a CRM system to integrate the forms data fields into its desired form.

In another group of embodiments of the invention, the merchant may simply use the merchant interface to indicate the forms data values (15) that appear on a form, and save this information in the on-site forms database (22) or pre-loaded forms database (20) instead of saving the form itself. Then, when the merchant asks a consumer to allow access to the consumer's forms data, the forms signer will search those tiers in the consumer's forms data, to which the consumer has allowed access, and find the forms data fields that correspond to the forms data values (15) that the merchant has indicated would be needed to fill out this particular form (Designated by the Form ID Code or Barcode Matrix Form ID Code). Then, the merchant API will return these forms data fields to the merchant, and the merchant will use a CRM system to import them into the desired form.

It is important to note that when the forms signer searches the tiers for forms data fields, the forms signer may do so, in some embodiments, by searching for the forms data groups to which these forms data fields belong, and returning every forms data field that is within the desired forms data group. These forms data fields can then be transmitted to the merchant or imported into a copy of the desired form, as discussed herein. It is also important to note that one potential method for the forms signer to determine which forms data fields are responsive to a forms data value (15) is for the forms signer to include information about which forms data groups are responsive to that forms data value (15), and to return all the forms data fields within these forms data groups. These forms data fields can then be transmitted to the merchant or imported into a copy of the desired form, as discussed herein.

In some embodiments, the invention will rely on a mapping feature, which is part of the forms signer, to fill out a form that has been placed in the pre-loaded forms database (20). In some embodiments of the invention, the merchant will have previously designated the forms data field or forms data groups that are responsive to each pre-designated form. The merchant can use the form identifier code (Form ID Code (11) or Matrix Barcode Form ID Code (12) in some embodiments) to identify, and search for, this type of form in the future. In still another embodiment of the invention, the forms signer associates a code (which can be a Form ID Code (11) or Matrix Barcode Form ID Code (12)) for a form with a group of form data values (15) required to complete that form.

In most embodiments, the forms signer only gives to the merchant information that is responsive to the forms data values (15) in the form, or forms data values (15) that the merchant has specifically asked for. In another group of embodiments, the forms signer uses the merchant API to simply return to the merchant all the forms data values in the tiers to which the consumer has consented release.

In this application, the term "form ID" means either a Form ID Code (11) or Barcode Matrix Form ID Code (12), unless otherwise explicitly designated. Both a Form ID code and a Barcode Matrix Form ID Code can fulfill the purpose of being unambiguous identifiers of types of forms. Furthermore, a form can have both a Form ID code and a Barcode Matrix Form ID Code without in any way detracting from the function of the invention. Therefore, whenever, in the specification of this application, it is stated that either a Form ID Code (11) or a Barcode Matrix Form ID Code is used, it is understood that this can indicate that either or both of these codes is used.

The Offline Forms Transposer

The offline forms transposer (23) is a sub-component of the invention, in certain embodiments of the invention without a dedicated merchant interface, an on-site forms database (22), or a pre-loaded forms database (20). The offline forms transposer (23) transposes the forms data fields that have been returned by the merchant API, in these embodiments, to a form that has been selected by the user after the merchant API has returned this information. The offline forms transposer (23) uses optical character recognition, or the other methods described herein, to determine which of the forms data fields returned by the merchant API should be placed into each of the forms data values (15) in the form. Essentially, the merchant selects a form file, using the offline forms transposer (23), and the offline forms transposer transposes the relevant forms data fields into the forms data values on the form. A copy of the altered form file can then be saved.

In other embodiments of the invention, the structure of the consumer response code (24) will itself indicate the form data values that are part of the form that needs to be filled out. Therefore, when the consumer app (2) takes a picture of the consumer response code, converts the picture into a data stream and sends this data stream to the transaction listener, the data stream will contain information identifying the forms data values that are part of the desired form. In effect, the picture of the consumer response code (24), which will be converted to a data stream, will show the forms data values that the form contains. The transaction listener will then be able to discern exactly which forms data fields are required to fill out these forms data values, and will be able to communicate with the forms signer and tell the forms signer to search the forms data storage for these specific forms data fields. The forms signer, alternatively, can discern which forms data fields are responsive to these forms data values.

Protocols by which a Merchant Conveniently Accesses the Consumer's Forms Data

The consumer will encounter merchants, who will ask the consumer to fill out forms. The consumer will then send some or all of the tiers (5) containing the consumer's pre-saved forms data to the merchant, using the invention, and the consumer will thus save time and avoid the possibility of errors. The invention can be used by merchants who wish to create purely electronic forms, or merchants who wish to create paper forms and print them. The invention can be used to create both kinds of forms.

In the first embodiment of the invention, when the consumer wants to send forms data to a merchant, the consumer and the merchant will begin the process when the merchant requests the consumer's forms data, within certain "tiers" (Tiers 1-3, Tiers 1-4, etc.) from the consumer's Online Profile (4). The merchant may also request certain specific data (One example is information about the consumer's past illnesses). The merchant will use the merchant interface (18) to do this. The merchant interface (18), in most embodiments, will tell the merchant the types of information that are listed in each tier, so the merchant can determine which tiers of information he or she needs. The merchant interface might do this via a list that is periodically updated using the internet. The merchant will then use the merchant interface (18) to send a request over the internet to the Central Server (16), for the forms data falling into certain tiers, and belonging to the specific consumer discussed above. The Request Service (17) would then create a transaction ID, and would create a transactional external identifier code and a transaction listener for that transaction. The Request Service (17) will also cause the form signer to send a notification to the consumer's designated consumer device (1). Then, the consumer will receive a notification on his consumer device (1), saying that the merchant has requested data in certain specified tiers from the consumer. This notification may be via text message, via a message that is part of the consumer interface in the App or other browser interface, via a "push" notification, via an "alert" or via another method. The consumer will then respond to the notification, saying that he or she gives permission to release the information in the requested tiers, to that specific merchant discussed above. The consumer will have to identify himself using two-factor authentication or other multi-factor identification, as discussed above. In the first embodiment, the consumer will use the consumer program (2) to do this. This information is sent from the consumer device (1) to the central server (16), and is received by the transaction listener (3). The transaction listener then informs the forms signer that the request has been authenticated, and the forms signer queries the forms data storage for all forms data within the selected tiers. A copy of the forms data within the selected tiers that is responsive to the forms data values of the merchant's request then appears on the screen of the consumer device (1). This information will be grouped into the form data fields responsive to each forms data value (15). Next to each forms data field, there will be a box which can be checked or unchecked, or another item which indicates whether the consumer desires to release that specific forms data field to the merchant. If the box is checked, this gives consent for the consumer to release the form field within that specific forms data value to the merchant.

All such boxes related to all forms data values (15) shall be checked when the copy of the forms data to be sent appears on the screen of the consumer device (1). If the consumer does not wish a specific item to be shared with the merchant, the consumer can "uncheck" the box for that forms data field, using methods that are known in the prior art. Then, that specific item, or forms data field will not be shared with the merchant. The consumer device then sends a notification to the central server indicating the types of information of which the consumer has authorized release to the merchant. The forms signer then sends the consumer's forms data from the relevant tiers to the merchant. The information is incorporated into the merchant's forms at this point, and the merchant may print out these forms or keep them in a computerized format.

The transaction ID (6) and external transaction identifier (19) can be alphanumeric codes, or matrix barcodes or QR codes, or other types of codes.

In one group of embodiments of the invention, the information is incorporated into the merchant's forms by the merchant interface (18).

In another embodiment of the invention, the merchant interface (18) will include an on-site forms database (22) of the merchant's forms, which will have been loaded into the merchant interface by the merchant. The merchant will previously have indicated, within the merchant interface, the type of form data that should be indicated in response to each question on the user's form. For example, the merchant will have indicated the question on the merchant's form where the appropriate response is the consumer's name, the question on the merchant's form where the appropriate response is the consumer's social security number, etc. The merchant interface will then transpose the consumer's name and other relevant form data to the appropriate places on the merchant's form, when the merchant receives the consumer's forms data.

In another embodiment of the invention, the central server will have a database of forms, including forms created by the merchant, (the Pre-Loaded Forms Database (22)), and the merchant will have previously designated the type of information that is supposed to be placed in each forms data value (15) of each form within the database pertaining to that merchant's Pre-Loaded Forms Database (22). The form signer will then place the correct information within each forms data value (15), and send the completed form to the merchant.

The notification service informs the consumer and the merchant when A) The consumer gives permission to the invention to send the relevant information, and B) when the invention sends the relevant information to the merchant. The notification service can also provide notifications at other points in the process.

In another embodiment of the invention, the external transaction identifier code is not created, and the transaction ID is the only unique identifier for the transaction. Therefore, the transaction ID is sent to the consumer device, and the transaction ID is what the consumer will use to give the invention permission to share his or her forms data with the merchant.

In embodiments of the invention that do not use an external transaction identifier code, the consumer response code (24) can include information that codes for the transaction ID and other information. In embodiments of the invention that do use an external transaction identifier code, the consumer response code (24) can include information that codes for the external transaction identifier code, and other information.

In another group of embodiments of the invention, there will not be a merchant interface. The merchant will request forms data from the central server (16) by communicating with the central server via email, text message, telephone, or another method that does not require a merchant interface. Forms data will be sent to the merchant via the internet, and will automatically populate the merchant's forms.

In still another group of embodiments of the invention, the merchant interface and consumer program will be different modules of the same "app" which both merchants and consumers can download. Therefore, an individual can use this app to act as a merchant in one transaction and act as a consumer in a different transaction.

It is also possible to build an embodiment of the invention that has one of these characteristics and also has the characteristic that the request service, form signer, and notification service, and any transaction listener, are subcomponents of a central program (21), and the embodiment does not involve a central server.

More Information about Certain Types of Transactions

In some embodiments, the merchant will have previously imported certain forms into the invention, and will include a code (either (11) or (12)) for each form. Then, when the merchant wants to initiate a transaction, the merchant will send the request, including the type of form, to the request service, and the request service will send back the consumer response code (24), which includes data that codes for the kind of form, and additional data that codes for the individual transaction. This additional data can be the transaction ID or external transaction identifier code in certain embodiments of the invention. The request service will also create a transaction listener that includes the information that codes for the transaction and form. The merchant will then display this consumer response code (24), which will be scanned by the permission feature of the consumer program (2) by the consumer. The consumer program will then convert the consumer response code (24) to a data stream and send this data stream to the transaction listener. The transaction listener will recognize the data stream, based on the parts of the data stream that code for the transaction and the type of form. The transaction listener will then know that the consumer has agreed to release of this data to the merchant.

The transaction listener will then communicate this to the notification service, which will notify all parties via "push" notifications, or text messages, or alerts, or another method.

The transaction listener will also communicate this to the forms signer. The forms signer will search the pre-loaded forms database (20) of the merchant to locate the form which the code (11) or (12) indicated that the merchant wished for the consumer to sign. Then, the forms signer will locate this form, and the forms data values (15) for this form will previously have been determined, and stored, in the pre-loaded forms database (20). They will have been determined via OCR or another one of the methods listed here. The forms signer will determine whether the forms data groups (or forms data fields) that are responsive to these forms data values belong to certain tiers. Then, the forms signer will inform the transaction listener to send a notification, via text, alert, push notification, or another method, to the consumer program (2) of the consumer, asking for permission for the merchant to have access to the tiers of data that the forms signer has identified. The consumer grants permission. This is sent to the transaction listener, which informs the notification service and forms signer. The notification service informs all parties that the consumer has granted permission for the merchant to have access to the forms data in certain tiers. The forms signer then searches the tiers of the consumer's Online Profile, that the consumer has granted access to, for the relevant forms data fields. The forms signer then inputs the relevant forms data fields into the form that the merchant desires the consumer to fill out. The forms signer then sends this completed form to the merchant, who may receive the completed form in a PDF, via email, or may receive it through the form being delivered directly to the merchant interface of the merchant, or the merchant may receive the completed form in another manner.

In another group of embodiments, which does not include the pre-loaded forms database, the forms signer may not import the relevant forms data into a copy of the needed form. Instead, another database such as the on-site forms database (22) or pre-loaded forms database (20) might include a record of the forms data values (15) in the desired form. This means that the database containing the record of the forms data values (15) might keep a record that the identified form includes forms data values for "name", "address", and whatever other forms data is desired. This database will not include a copy of the form itself, however.

The record of the needed forms data values (15), or of the desired forms data groups or forms data fields, will be found by the forms signer, which will search the pre-loaded forms database, or found by the request service, in embodiments where the request service searches the pre-loaded forms database (20). The forms signer will search the tiers (5) in the consumer's Online Profile (4) for this information. The forms signer will determine whether the forms data groups (or forms data fields) that are responsive to these forms data values (15) belong to certain tiers, based on records contained within the forms signer. These records will discuss the forms data groups that are incorporated in each tier. Then, the forms signer will inform the transaction listener to send a notification to the consumer program (2) of the consumer, asking for permission for the merchant to have access to the tiers of data that the forms signer has identified. The consumer grants permission. This permission is sent to the transaction listener, which informs the notification service and forms signer. The notification service informs all parties that the consumer has granted permission for the merchant to have access to the forms data in certain, specified, tiers. The forms signer then searches the tiers of the consumer's Online Profile, that the consumer has granted access to, for the relevant forms data fields. The forms signer locates these forms data fields and sends them to the merchant via a merchant API, which then makes these forms data fields available to the merchant to incorporate into its forms via a CRM program.

In some embodiments within this category, there is no pre-loaded forms database (20) and the relevant forms data values (15) for the desired form are stored within the on-site forms database (22).

In still another group of embodiments, the consumer response code (24) that is sent by the request service to the merchant interface will include information about the forms data values, forms data groups, or forms data fields that are required by the merchant to fill out the desired form. The consumer will scan this consumer response code (24) and send it to the transaction listener (3) in the manner mentioned above, and the transaction listener (3) will inform the forms signer that the consumer has consented to release of the specific information in those forms data groups, or forms data fields, or which will fill the specific, desired forms data values (15) in the form requested by the merchant. The forms signer will then search the tiers in the consumer's online profile (4) for the relevant information, and will deliver this information to the merchant via a merchant API. The merchant will then use a CRM system to incorporate this information into the merchant's forms.

In a related group of embodiments, the merchant will be able to custom-select the forms data groups, forms data fields, or forms data values that the merchant desires, by initiating a transaction by sending a message to the request service with this information. The request service will then send back a consumer response code (24) that will include information about the forms data values, forms data groups, or forms data fields that are required by the merchant to fill out the desired form, and the transaction will proceed, as noted above.

In some embodiments, the merchant can input information about the forms data values (15), forms data groups, or forms data fields that are required for each form, into the databases (22) or (20), without uploading the forms themselves into databases (22) or (20) or determining the forms data values needed to fill out these form. Therefore, if a merchant knows that a specific form will require a consumer's name, address, and phone number, the merchant will input into the on-site forms database (22) that the form will require the forms data fields for the consumer's name, address, and phone number. Then, the transaction will proceed in one of the appropriate methods discussed herein.

The merchant can also use the forms data to do CRM analysis. In some embodiments, the merchant will have previously imported certain forms into the invention, and will include a code (11) or (12) for each form. Then, when the merchant wants to initiate a transaction, the merchant will send the request to the request service, including information about the type of form desired. The request service will send back the consumer response code (24), which includes data that codes for the type of form desired, and data that codes for the individual transaction. This data can be the transaction ID or external transaction identifier code in certain embodiments of the invention. The request service will also create a transaction listener that includes information that codes for the transaction and type of form desired. The merchant will then display the consumer response code (24), which will be scanned by the consumer program (2) by the consumer. The consumer program will then convert the consumer response code (24) to a data stream and send this information to the transaction listener. The transaction listener will recognize the data stream, based on the parts of the data stream that code for the transaction and the type of form. The transaction listener will then know that the consumer has agreed to release of this data to the merchant. The transaction listener will then communicate this to the notification service, which will notify all parties via "push" notifications. or text messages.

The transaction listener will also communicate this to the forms signer. The forms signer will search the pre-loaded forms database (20) of the merchant to locate the form which the code (11) or (12) indicated that the merchant wished for the consumer to fill out. Then, the forms signer will locate this form, and the forms data values (15) for this form will previously have been determined, and stored, in the pre-loaded forms database (20). They will have been determined via OCR or another one of the methods listed here. The forms signer will determine whether the forms data groups (or forms data fields) that are responsive to these forms data values belong to certain tiers. Then, the forms signer will inform the transaction listener to send a notification to the consumer program (2) of the consumer, asking for permission for the merchant to have access to the tiers of data that the forms signer has identified. The consumer grants permission. This is sent to the transaction listener, which informs the notification service and forms signer. The forms signer informs all parties that the consumer has granted permission for the merchant to have access to the forms data in certain tiers. The forms signer then searches the tiers of the consumer's Online Profile, that the consumer has granted access to, for the relevant forms data fields. The forms signer then inputs the relevant forms data fields into the form that the merchant desires the consumer to fill out. The forms signer then sends this completed form to the merchant, who may receive the completed form in a PDF, via email, or may receive it through the form being delivered directly to the merchant interface of the merchant, or the merchant may receive the completed form in another manner.

The merchant then uses a CRM program to perform various types of analysis on the forms that have been received from various consumers.

In another embodiment, which does not include the pre-loaded forms database, the forms signer may not import the relevant forms data into a copy of the needed form. Instead, another database might include a record of the forms data values (15) in the desired form. The record of the forms data values (15), or of the desired forms data groups or forms data fields, will be found by the forms signer, and the forms signer will search the tiers in the consumer's profile for this information. The forms signer will determine whether the forms data groups (or forms data fields) that fulfill these forms data values belong to certain tiers, based on records contained within the forms signer of the forms data groups that are incorporated in each tier. Then, the forms signer will inform the transaction listener (3) to send a notification to the consumer program (2) of the consumer, asking for permission for the merchant to have access to the tiers (5) of data that the forms signer has identified as containing the needed forms data fields. The consumer grants permission. This permission is sent to the transaction listener (3), which informs the notification service and forms signer. The forms signer informs all parties that the consumer has granted permission for the merchant to have access to the forms data in certain tiers (5). The forms signer then he searches the tiers of the consumer's Online Profile, that the consumer has granted access to, for the relevant forms data fields. The forms signer locates these forms data fields and sends them to the merchant via a merchant API, which then makes these forms data fields available to the merchant to incorporate into its forms via a CRM program.

In still another group of embodiments, the consumer response code (24) that is sent by the request service to the merchant interface will include information about the forms data values, forms data groups, or forms data fields that are required by the merchant to fill out the desired form. The consumer will scan this code and send it to the transaction listener in the manner mentioned above, and the transaction listener will inform the forms signer that the consumer has consented to release of the specific information in those forms data groups, or forms data fields, or which will fill those specific forms data values. The forms signer will then search the tiers in the consumer's online profile for the relevant information, and will deliver this information to the merchant via a merchant API. The merchant will then use a CRM system to incorporate this information into the merchant's forms.

In a related group of embodiments, the merchant will be able to custom-select the forms data groups, forms data fields, or forms data values that the merchant desires, by sending a message to the request service with this information. The request service will then send back a consumer response code (24) will include information about the forms data values, forms data groups, or forms data fields that are required by the merchant to fill out the desired form, and the transaction will proceed, as noted above.

Some consumers may be worried that the present invention will make identity theft easier, but a large amount of consumers' personal data, including most or all of the forms data stored in the forms data store, is presently online in various databases anyway. The present invention will help to catch and prosecute identity thieves, because each time any part of a consumer's forms data is sent to a merchant, the invention will keep the transaction ID of the transaction and a record of the merchant who requested the transaction. Therefore, if a consumer believes their identity has been stolen and tries to catch the thief, the consumer will have a record, created by a third party, of all the merchants who have downloaded the consumer's forms data, which the consumer or police can use as the starting point for the investigation.

In addition, highly sensitive data can be stored in an encrypted format, to prevent unauthorized release of that data. In some embodiments of the invention, a consumer will only be able to consent to the release of this data by entering a passphrase from memory, or via secure storage, such as, but not limited to, Touch ID or Secure Enclave, on the consumer's mobile phone.

The first embodiment of the invention allows access to each "tier" of information to be inclusive of access to the information in lower-level tiers. However, in another version of the invention this will not be the case, and access to each tier of information will only allow the merchant to see information within that tier.

In some implementations of the invention, when the consumer decides that he wants to release information to the merchant, and decides what tiers he wants to release information for, the user is presented with a screen that has a checked box next to each piece of information in each tier. The user can simply release all the information in the affected tiers, or uncheck some of the boxes and choose not to release the information next to the unchecked boxes, but release the information next to the checked boxes.

In another embodiment of the invention, the user can customize the types of forms data included in each tier of information. In other words, the consumer can customize the "theme" of each tier (5), because the tiers will be organized thematically. This may be counterproductive, though, because it would mean that the consumer would have to do more work, to cause forms data to be sent to a merchant, than the consumer would have to do otherwise.

In the first embodiment of the invention, if the consumer consents to releasing the forms data in any one tier to the merchant, the consumer also consents to the release of the forms data in all lower tiers to that merchant. For example, if the consumer consents to release of the forms data in tier 6 to a merchant, he also consents to the release of the forms data in tiers 1-5 to that merchant. However, there is another embodiment of the invention where, if the consumer consents to releasing the forms data in any one tier to the merchant, the consumer does not consent to the release of the forms data in any lower tiers to that merchant. Therefore, in this second embodiment, if the consumer consents to release of the forms data in tier 6 to a merchant, he does not automatically consent to the release of the forms data in tiers 1-5 to that merchant.

Any information that is in the tiers of information requested by the merchant, that is not responsive to one of the forms data fields (15) on the form, will not appear on the form.

In versions of the invention where the merchant interface queries the transaction signer for only certain specific information from the relevant tiers, the other information in the relevant tiers will not be incorporated into the form.

Example of a Merchant's Use of the Electronic System and Method to Quickly Fill Out a Form for a Consumer Here is one example of a transaction between a merchant and a consumer in an embodiment of the invention through which the merchant has previously uploaded forms into a Pre-loaded forms database (20), and where an external transaction identifier code is not utilized. The merchant begins the transaction by contacting the request service, asking to acquire a specific consumer's form data to fill out a specific type of form. The specific type of form will be identifiable by a Form ID Code, and will request certain information, which will be in certain tiers. The types of information requested by that form, and the form data fields (15) in that form, will have been determined previously, when the form was uploaded.

The request service then creates the transaction listener, which has the ability to exchange information with the request service, forms signer, and notification service. The request service will also create the transaction ID for the transaction. The request service also communicates with the form signer, which queries the forms data storage to determine the identity of the tiers of information that must be released to complete this form. This information is sent to the transaction listener.

The transaction listener then communicates with the notification service, and the notification service informs the consumer that the merchant has requested information in certain specific tiers. The consumer then uses his or her device to communicate consent to the transaction listener, and the transaction listener transmits this information to the forms signer and notification service. The notification service then informs the consumer and merchant that the consumer has consented to the release of information.

The forms signer then queries the forms data storage for the forms data fields within the relevant forms data groups, in the tiers of information that the consumer has consented to be released, that can be used to fill out the form. The notification service sends all parties an alert that this is happening. The forms signer then imports the relevant information needed to fill out the form into a copy of the form that the forms signer has acquired from the pre-loaded forms database. The forms signer does this by reviewing the information in the relevant tiers, and extracting the forms data fields that fall within the forms data groups that match the forms data values requested by the form.

Then, the forms signer sends this completed form to the merchant, which can receive it via its CRM, by email, or in another manner. The forms signer also sends the transaction listener and notification service a message saying that the completed form has been sent to the merchant.

The notification service sends the consumer and merchant a message saying that the relevant form has been sent to the merchant. The transaction data store is updated. The transaction listener is then closed.

In most embodiments of the invention, information that in the tiers searched by the forms signer, but is not responsive to one of the forms data values (15) on the form, will simply not be released to the merchant. Only forms data fields that are specifically responsive to a request by the merchant will be returned to the merchant.

The MiFi Rewards Program

There is another category of embodiments of the invention, where the merchant displays a consumer response code (24), and the consumer can, at his or her leisure, use the consumer program (2) to take a picture of the code and initiate a transaction.

One example is the MiFiMat program.

The "MiFiMat" program is based on an invention disclosed in a provisional patent, in 2013, by Thomas Ralph Rossi, one of the inventors herein. Variations of the MiFimat are useful extensions of the current invention. In one variation, a merchant will prominently display a code such a consumer response code (24), on a mat. A consumer can stand on the mat and use the consumer program (2) to scan the consumer response code. The consumer response code will be configured to indicate that the consumer who scans it with the consumer program (2) wants to fill out a specific type of form, with a specific form ID code or Barcode matrix form ID code. The consumer program (2) will then convert the consumer response code (24) to a string of data and send the data from the code to the request service. This will start a transaction. After the transaction is started, the transaction will then proceed in a similar manner to the merchant-initiated transactions discussed above, after the transaction is started. The request service will create a transaction listener, and communicate with the notification service and the form signer. The consumer will send a confirmation to the transaction listener that he or she wants to release specific forms data to the merchant. The forms signer will then query the forms data storage in the consumer's Online Profile, and will send the relevant forms data to the merchant. The merchant can then use this forms data to fill out one of its forms, using one of the manners discussed herein.

The merchant can display a code such as the consumer response code (24), on other objects besides the mat. For example, the merchant can display a consumer response code on a banner. Then a consumer can scan the banner the way he or she would scan the MiFiMat.

This system opens up numerous additional possibilities for the merchant. The merchant can make specific or more general offers, where the consumer may need to release to the merchant specific forms data fields in order to take advantage of the offer. An example might be a merchant offering "0% financing on clothes" to people who sign up for a store credit card. In order to take advantage of this offer, a consumer will have to release, to the merchant, enough forms data for the merchant to make a reasoned consideration of the consumer's store credit card application. A consumer who encounters this offer can decide to take advantage of the offer, there and then, without having to find a store employee who may have paper credit card applications. The consumer can release information within certain tiers (5) of his profile (4) to the merchant, and then the merchant will receive those forms data fields that are responsive to the merchant's credit card application. The merchant will then be able to make a credit decision electronically, within seconds.

The merchant can also prominently display a code such as the Form ID Code (11) or Barcode Matrix Form ID Code (12), which consumers can scan with their cellular phones. The consumer will use the consumer program (2) on his cellular phone to scan the code, and send the data, to which the scan has converted, to the request service. In some embodiments, the data stream will contain information about the forms data values (15) that are part of the desired credit card application form. The request service will then create a transaction listener, and the transaction will proceed like a consumer-initiated transaction above. This will allow the consumer to quickly indicate his interest in the offer, and to send the information needed for evaluation of his credit card application, to the merchant.

The merchant will then also have possession of some of the consumer's forms data, and can use this information to create offers that are custom-tailored to that particular consumer or to people similar to that particular consumer. These offers can be sent to the consumer by text message, email, push notification, "alert", or whatever other method will accomplish the desired goal.

A merchant can use a CRM system to analyze this forms data and create such custom offers more easily. The merchant can theoretically do this in real time. For example, a jewelry merchant in a shopping mall who discovers that people who purchased ruby earrings on a certain day tend to have certain characteristics, through analysis of their forms data, might send those people an "alert" containing a custom offer for ruby bracelets later on the same day. Alternatively, the jewelry merchant might collaborate with a restaurant in the shopping mall to send those individuals who purchase ruby earrings on a particular day an "instant offer" from the restaurant, for a half-price dish, to be consumed on that day. If the restaurant is a 10-minute walk away from the jewelry store, the offer can be timed to appear on consumer's consumer devices 10 minutes after the consumers conclude their purchases at the jewelry store.

A Simplified Method of Using the Vital Data Assistant System

The Vital Data Assistant system, or "VDA system", was created by Thomas Rossi, one of the inventors herein, and is the subject of patent application Ser. No. 14/617,355. The present invention simplifies the method of using the Vital Data Assistant system in the following manner:

A person sometimes signs up for the Vital Data Assistant system by buying one or more "VDA medallions", and associating the QR codes on these VDA medallions with an online profile, in which the person inputs various kinds of information pertaining to the individual's health and other matters. More information about this is included in application Ser. No. 14/617,355.

The present invention allows the user (A consumer, in this case) to sign up for the Vital Data Assistant system by using the consumer program (2) to scan a specially designed QR code, (a consumer response code (24)) on a VDA medallion, and send this consumer response code to the request service of the present invention. The consumer can then give consent for the consumer's forms data, in certain tiers, to be imported by the forms signer to a form taken from a pre-loaded forms database (20) controlled by the Vital Data Assistant invention. This form, combined with the forms data imported from the tiers in a consumer's online profile, will then be saved by the Vital Data Assistant invention in one of its databases. The consumer can therefore much more easily give the Vital Data Assistant invention the information that the Vital Data Assistant invention needs to serve the consumer.

This method is much simpler, and more convenient, for the consumer, than typing out the information about a consumer's health conditions, required for a consumer to most effectively use the Vital Data Assistant invention. Therefore, users of the present invention will be able to sign up for the Vital Data Assistant system much more easily.

Some More Potential Applications of the Invention

The invention will allow consumers to save a huge amount of time, which they presently spend filling out forms. Consumers will instead be able to import their previously saved forms data into the forms made by merchants. Among other uses, consumers will be able to fill out forms quickly when standing in line, and present those forms to a merchant's employees when they reach the end of the line. Furthermore, a merchant could potentially display a large consumer response code (24), in front of a long line of people, in lieu of giving the people a paper form which might be required for the people to fill out, to get help. The individuals in line could all scan the consumer response code (24) and use the present invention to fill out their forms before they reach the front of the line, thus saving them and the merchant's personnel a lot of time.

Consumers sometimes also experience problems caused by the fact that they may run out of space on a form, to transcribe certain categories of forms data. For example, a consumer filling out a paper form that asks for his "past addresses" might run out of space, on the paper, in which to place information about his past addresses. The present invention eliminates this problem. A consumer who has placed all of his past addresses in the initial form, filled out when the consumer created an Online Profile, can then give the relevant merchant access to the tier of data containing his past addresses, and thus avoid the problem of running out of space on a paper.

The functionality of this invention will provide huge labor savings to consumers and merchants, and will dramatically reduce errors in data collection.

Merchants can also benefit through greater data processing efficiency, which will reduce merchants' costs. Merchants will also benefit from increased sales in many cases. If consumers can fill out a merchant's forms more efficiently and quickly, this is a greater convenience for consumers, which allows those consumers to spend more time examining and purchasing the merchant's products.

In theory, two or more merchants could save a large amount of forms data about themselves, in Online Profiles regarding themselves, and could then exchange this forms data very quickly, for purposes such as supply chain management, and distribution, using the current invention. This opens up the possibility of new types of transactions between merchants.

For example, as information is placed in the tiers of one merchant's profile by that merchant's employees, this merchant can give permission to several other merchants to search tiers in the profile, and quickly gain access to this updated information. They can then make decisions that either help themselves, or help them to serve the first merchant, or both, more easily than they would be able to do otherwise.

The invention makes also makes digitization of medical records easier, for merchants in medical-related fields. Businesses in the medical field presently are experiencing pressure to "computerize" their medical records, and transcribe those medical records into digital format, to cut costs. The present invention makes this easier, because the forms (A type of medical record) filled out using the invention will already be in a digital format, when they are created. Therefore, these forms can easily be shared among medical providers, as necessary, which will be more convenient, and cheaper, for the medical providers.

The first embodiment of the invention can serve as a central "clearinghouse", or central application, which stores a variety of forms data, that pertains to many different kinds of forms, for consumers. Merchants and others can then build a wide variety of other applications that efficiently interact with the central application. These applications can interface with the central application and get needed data from the central application, to fill out forms. An example might be an application, created by a merchant, that receives a consumer's forms data within certain specific tiers, imports the forms data into the forms created by the merchant, and then performs calculations on the data in these forms, and displays the results of these calculations to the merchant. The consumers whose forms data is received by the merchant will previously have given permission for this, of course. This is not the only possible example of an application, customized for a merchant, that interacts with the invention.

The invention is also a potential substitute for business cards. When two individuals who desire to exchange contact information meet each other, each individual can act as a merchant and request access to the other's "tier 1" forms data. Then, each individual can act as a consumer and grant the other person access to his or her "Tier 1" forms data, or whatever other tier of forms data is appropriate. The forms data that the two individuals can allow each other to have access to will include contact information. Both individuals can then later use this contact information to contact each other. This also means that these two individuals will be able to avoid the problems associated with losing business cards belonging to other individuals, and running out of their own business cards.

Commentators have described "digital natives" as people who have had interaction with computer technology since a very young age. The current invention will appear to be intuitive to digital natives. The simplicity and ease-of-use of the invention will also make it useful to other consumers.

In one embodiment of the invention, the service will be made available to consumers, in exchange for a small fee paid when a consumer creates an Online Profile, and also a small transaction fee to the consumer for using the service.

The discussion included in this patent is intended to serve as a basic description. The reader should be aware that the specific discussion may not explicitly describe all embodiments possible, and alternatives are implicit, or obvious to those skilled in the art. Also, this discussion may not fully explain the generic nature of the invention and may not explicitly show how each feature or element can actually represent equivalent elements. Again, these are implicitly included in this disclosure. Where the invention is described in device-oriented terminology, each element of the device implicitly performs a function. It should also be understood that a variety of changes may be made to the embodiments that have been described, without departing from the essence of the invention. Such changes are implicitly included in the description. These changes still fall within the scope of this invention.

Furthermore, each of the various elements of the invention and claims may also be achieved in a variety of manners. This disclosure should be understood to encompass each such variation, whether it is a variation of an apparatus embodiment, a method embodiment, a system embodiment, or a variation in any element of an embodiment. As the disclosure relates to elements of the invention, the words describing each element may be replaced by equivalent apparatus terms, even if only the function or result is the same. Such equivalent, broader, or even more generic terms should be considered to be encompassed in the description of each element or action. Such terms can be substituted, when desired, to make explicit the implicitly broad coverage to which this invention is entitled. The reader should understand that all actions may be expressed as a means for taking the action in question, or may be expressed as an element for causing the action in question. Similarly, each physical element disclosed should be understood to encompass a disclosure of the action which that physical element facilitates. The reader should also understand that multiple programming languages may be utilized to construct the software components of the invention. Such changes and terms are to be understood to be explicitly included in the description.

BRIEF DESCRIPTION OF THE DRAWINGS

FIG. 2 shows an example of a screen which shows the data that the consumer is going to send to an automobile dealership for the purpose of securing an automobile loan. The boxes next to different types of information are checked, and the consumer can uncheck them if he wishes.

DETAILED DESCRIPTION OF THE DRAWINGS

Figure 1:
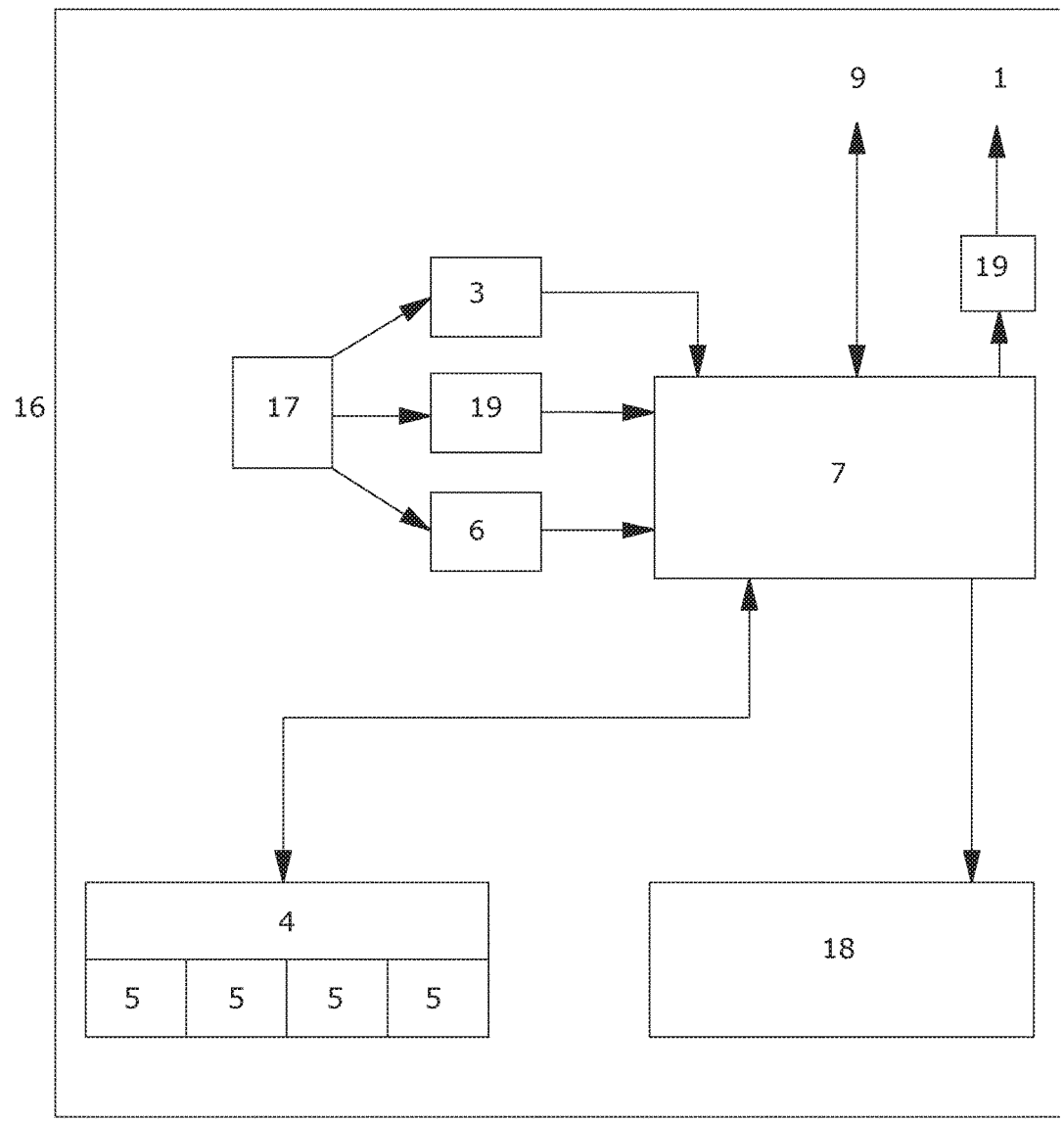
FIG. 1 shows a flow chart of what happens when a merchant requests a consumer's forms data from that user, and the user sends the forms data to the merchant using the first embodiment of the invention.

FIG. 1 shows a flow chart of one version of what happens when a merchant requests a consumer's forms data from that consumer, and the consumer sends the forms data to the merchant using one embodiment of the invention. First, the merchant requests forms data from a consumer using the merchant API (application program interface), by sending a request to the central server. The request will specify the tiers of data that the merchant is requesting (e.g. tiers 1-3, tiers 1-5, etc.). The request service receives the request, and then creates a transaction listener, transaction ID, and external transaction identifier code for the transaction. This information is then sent to the forms signer, which sends the external transaction identifier code to the consumer device (1). The consumer can then type in the external transaction identifier code when he or she wants to complete the form. When the consumer does this, the consumer's forms data in the requested tiers is displayed to the consumer, on the consumer device, and the consumer has an opportunity to "uncheck" each of the forms data values (15) that contains forms data values that the consumer does not want to send to the merchant. Then the consumer tells the consumer program (2) to send a notification to the form signer, indicating the form data that the consumer consents to release. Then the form signer sends this information to the merchant interface.

FIG. 2 shows an example of a screen which shows the data that the consumer is going to send to an automobile dealership for the purpose of securing an automobile loan. The boxes next to different types of information are checked, and the consumer can uncheck them if he wishes.

Figure 3:
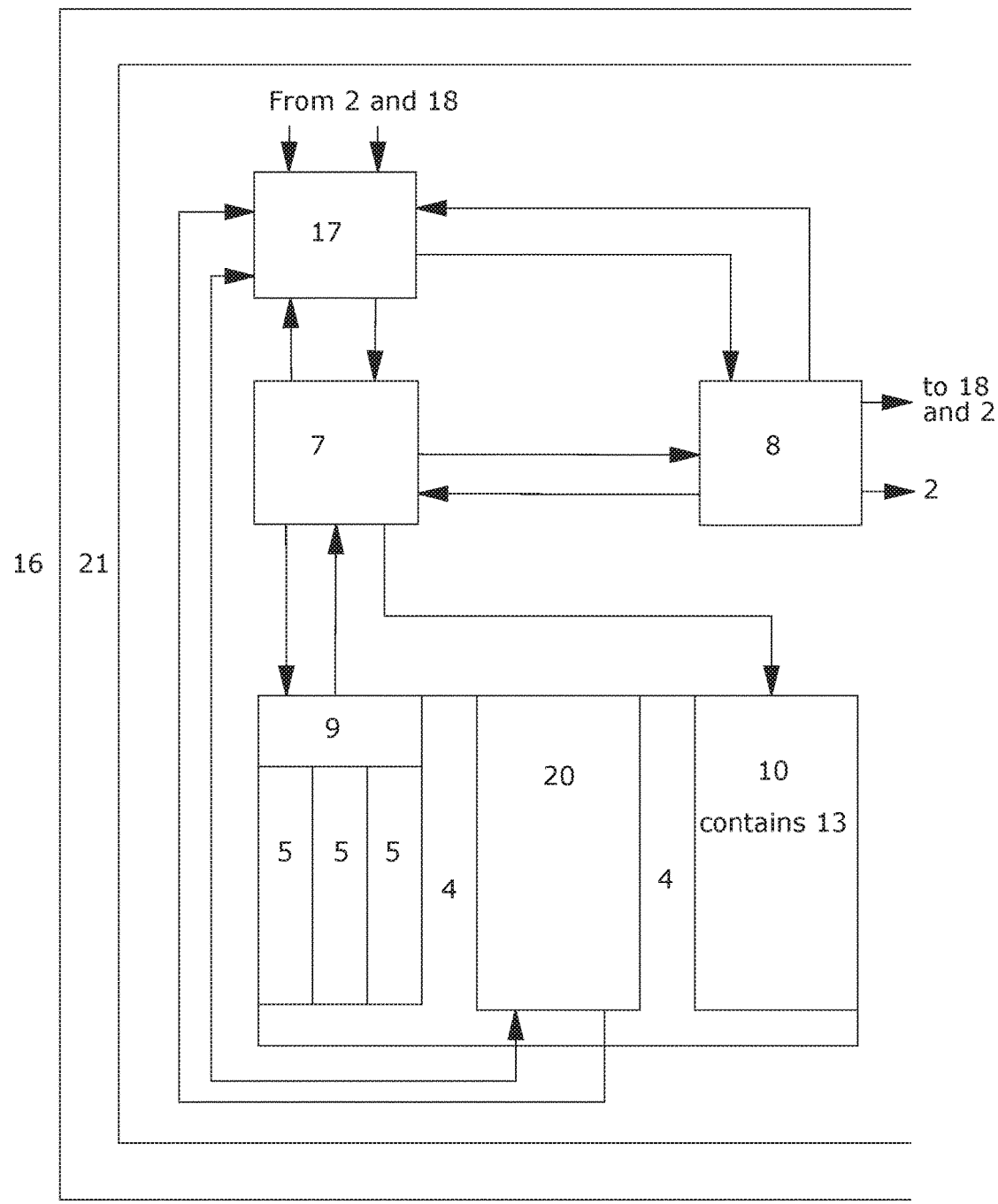
FIG. 3 shows an example of the relationship between different components of the invention, located on the central server, in the first embodiment.

FIG. 3 shows an example of the relationship between different components of the invention, located on the central server, in the first embodiment. In this embodiment, the transaction data storage (10), the forms signer (7), the Online Profile (4), the pre-loaded forms database (20), all tiers (5) in the forms data storage (9), the request service (17), and the notification service (8) are all part of the central program (21) which is stored on the central server (16). The forms data storage (9) and transaction data storage (10) are part of the Online Profile (4). The tiers (5) are part of the forms data storage (9). The notification service (8) communicates with the request service and forms signer, and any transaction listener, and informs them when it has sent notifications to one or both parties. The request service (7) creates the transaction listener, and also communicates with the request service and the forms signer. The forms signer communicates with the request service and notification service, and transaction listener, and sends the request service and notification service and transaction listener information about the progress of its searching the tiers in the forms data storage for the information desired by the merchant, which the consumer has given consent to release. The forms signer connects with the profile and searches the tiers in the profile, as part of a transaction.

Each transaction code (13) for a transaction that the consumer has engaged in, is stored in the transaction data storage (10).

Figure 4:
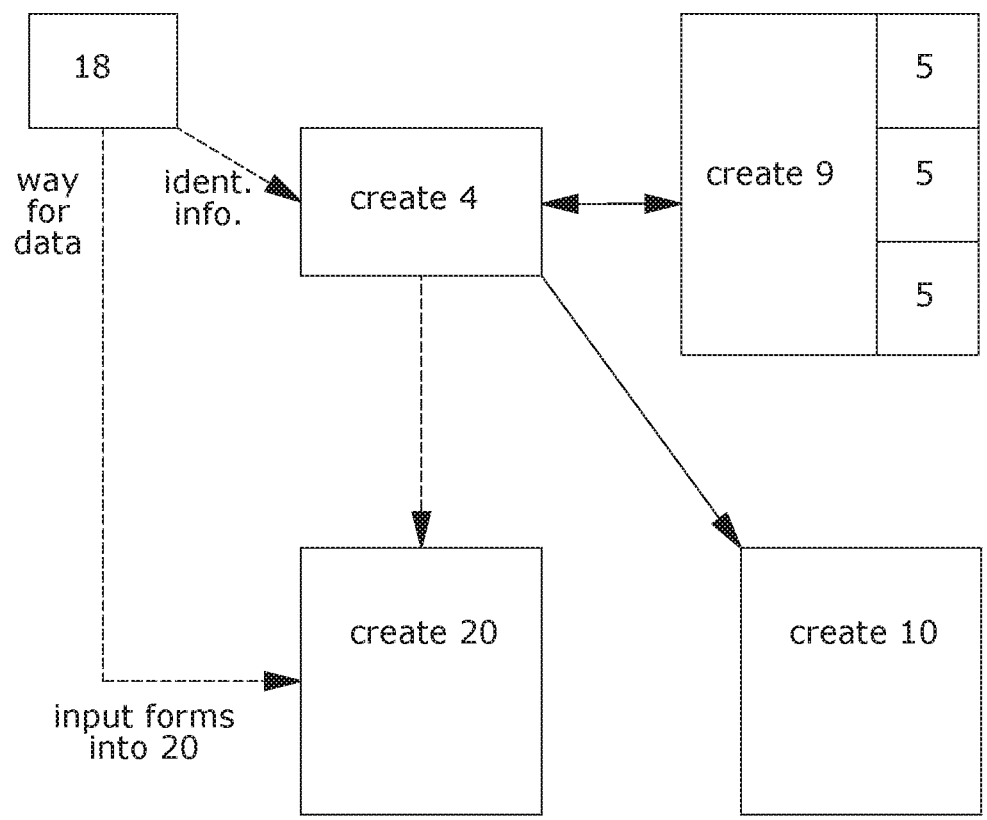
FIG. 4 shows a flow chart of, in one embodiment of the invention a merchant establishing an Online Profile with the invention, downloading the merchant interface, and uploading a group of forms to be filled out into the online database, part of the merchant's Online Profile, that contains the merchant's forms.

FIG. 4 shows the tasks in one embodiment of the invention which the different components of the invention perform when a merchant signs up for the invention and establishes an Online Profile so that the merchant can acquire forms data from consumers. First, the merchant accesses the merchant interface (18) and established an Online Profile, and, in so doing, includes identifying information, and authenticates the information and profile using two-factor authentication or other multi-factor identification. The merchant also specifies a way for the merchant to receive forms data from consumers. The merchant may also input its own forms data, and this forms data will be stored in tiers in the forms data storage for the merchant's Online Profile.

In this version of the invention, the merchant's Online Profile may include a pre-loaded forms database, and each type of form for which the merchant wants to input consumers' form data, will be included in the pre-loaded forms database. Each type of form will be given a Form ID Code or Barcode Matrix form ID code. Another embodiment would allow for direct data transfer via the Merchant API to directly populate the data into the merchant's business applications.

Once the merchant has established an Online Profile, the merchant has the ability to send the request service a message, requesting a consumer's forms data. The request service will then create a transaction listener and a transaction ID. After the merchant authenticates himself, the consumer authorizes the merchant to receive the consumer's forms data, by communicating with the transaction listener. The transaction listener then tells the forms signer to send the requested forms data to the merchant's Customer Relations Management system. The forms signer will access the consumer's Online Profile and scan the forms data storage for the information that is in the requested tiers. The forms signer will then send this information to the merchant.

Figure 5:
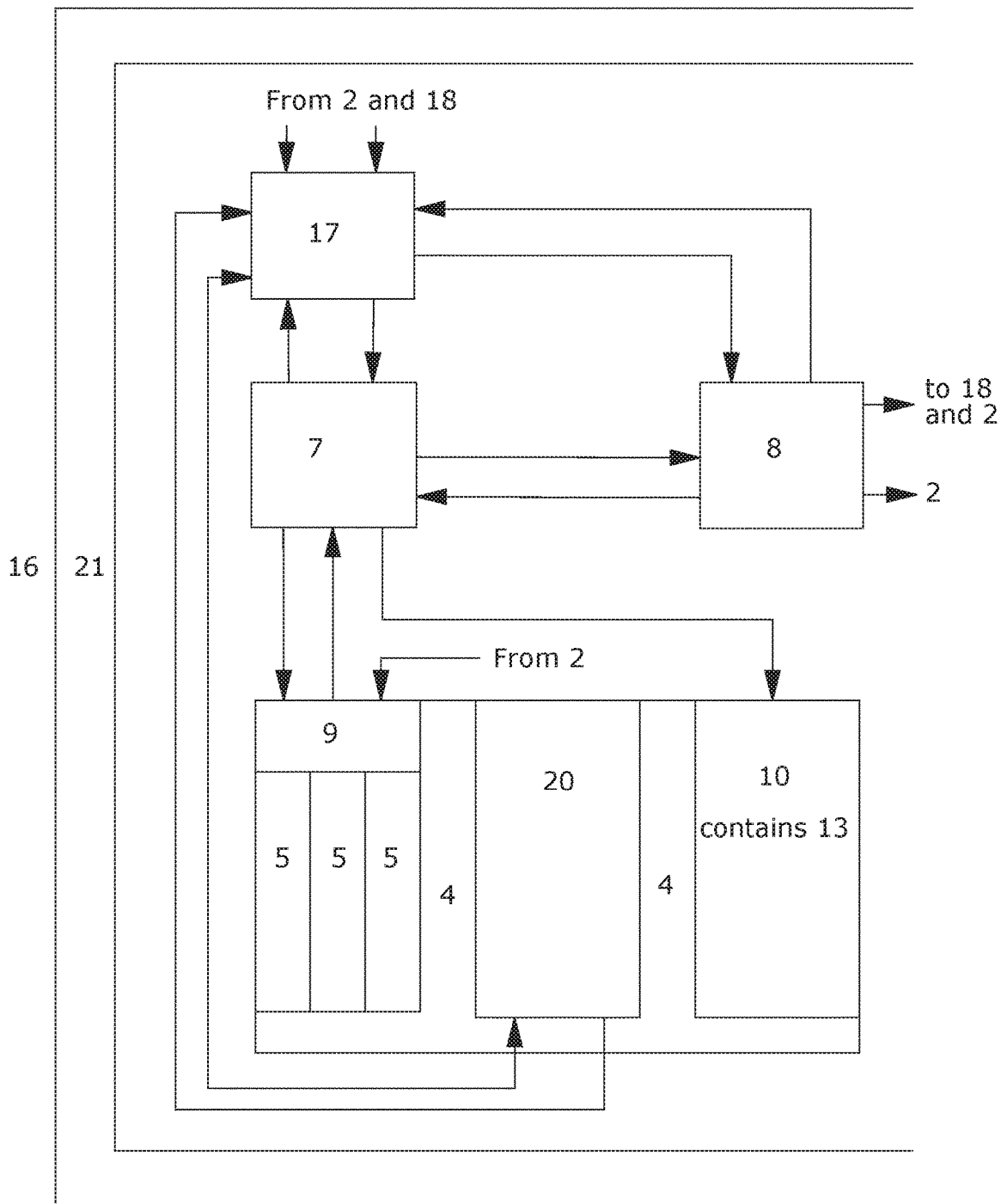
FIG. 5 shows, in one embodiment of the invention a flow chart of the actions which happen when a consumer creates an Online Profile and inputs form data into the Online Profile.

FIG. 5 shows, in one embodiment of the invention a flow chart of the actions which happen when a consumer creates an Online Profile and inputs form data into the Online Profile. First, the consumer authenticates herself. Then, an Online Profile is created, The Online Profile includes a transaction data storage, a forms data storage, and a pre-loaded forms database. The consumer then inputs her forms data into the initial form. The initial form saves this information into the forms data storage, where the forms data storage categorized this information into consumer-defined tiers. The form signer can then access this information when the consumer wishes to engage in a transaction with a merchant later.

Figure 6:
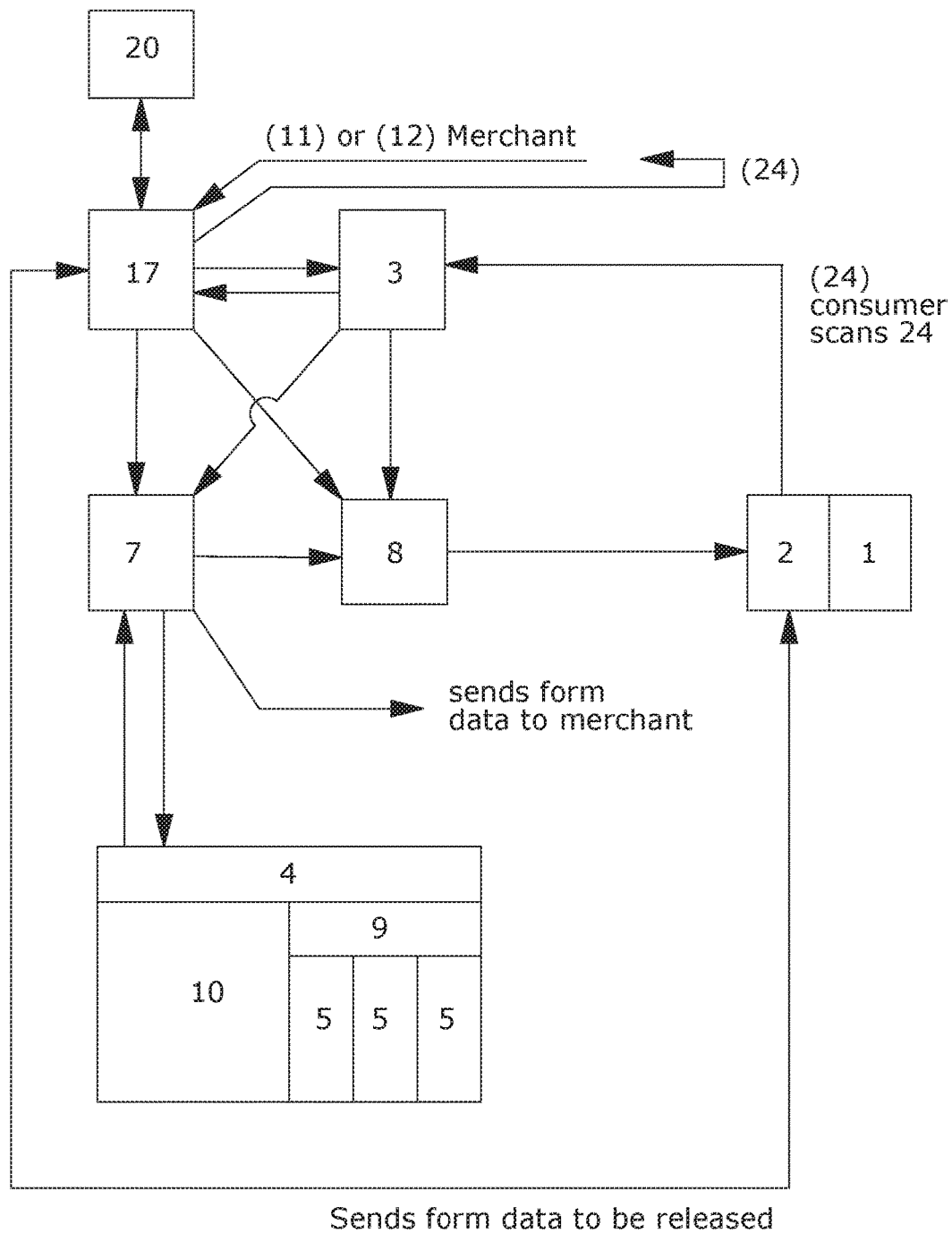
FIG. 6 shows the relationship between four of the different components of the invention, the forms signer (7), the request service (17), the transaction listener (3), and the notification service (8).

FIG. 6 shows the relationship between four of the different components of the invention, the forms signer (7), the request service (17), the transaction listener (3), and the notification service (8). In some embodiments of the invention, the merchant interacts with the request service (17), and starts a transaction by contacting the request service (17). The merchant includes the Form ID code (11) or Barcode Matrix Form ID code (12) and sends this to the request service (17). The request service (17) then creates a transaction listener (3). The request service (17) also searches the pre-loaded forms database (20) of the merchant, for the desired form, and determines the forms data values (15) that are a part of that form. The request service communicates this information to the forms signer (7). The request service (17) then informs the notification service (8) that the merchant desires to release the information in certain tiers (5) of forms data to the merchant. The notification service (8) communicates with the consumer program (2), which operates on the consumer device (1), and the request service informs the consumer program (2) that the merchant has requested that the consumer release forms data, within those specific tiers (5), to the merchant. The request service also sends a consumer response code (24) to the merchant, which displays the consumer response code (24) to the consumer. The consumer agrees to release of the forms data, by accepting the consumer response code (24) with the consumer program (2). The transaction listener then communicates the consumer's consent to release of forms data within specific tiers to the request service, notification service, and forms signer. The forms signer, searches the tiers of the forms data storage of the consumer's profile, which the consumer has consented to be searched. The forms signer finds the forms data fields that are needed to complete the forms data values (15) of the desired form. The forms signer then sends these forms data fields to the merchant into the form that has been requested. The notification service informs both parties that this form has been completed.

Figure 7:
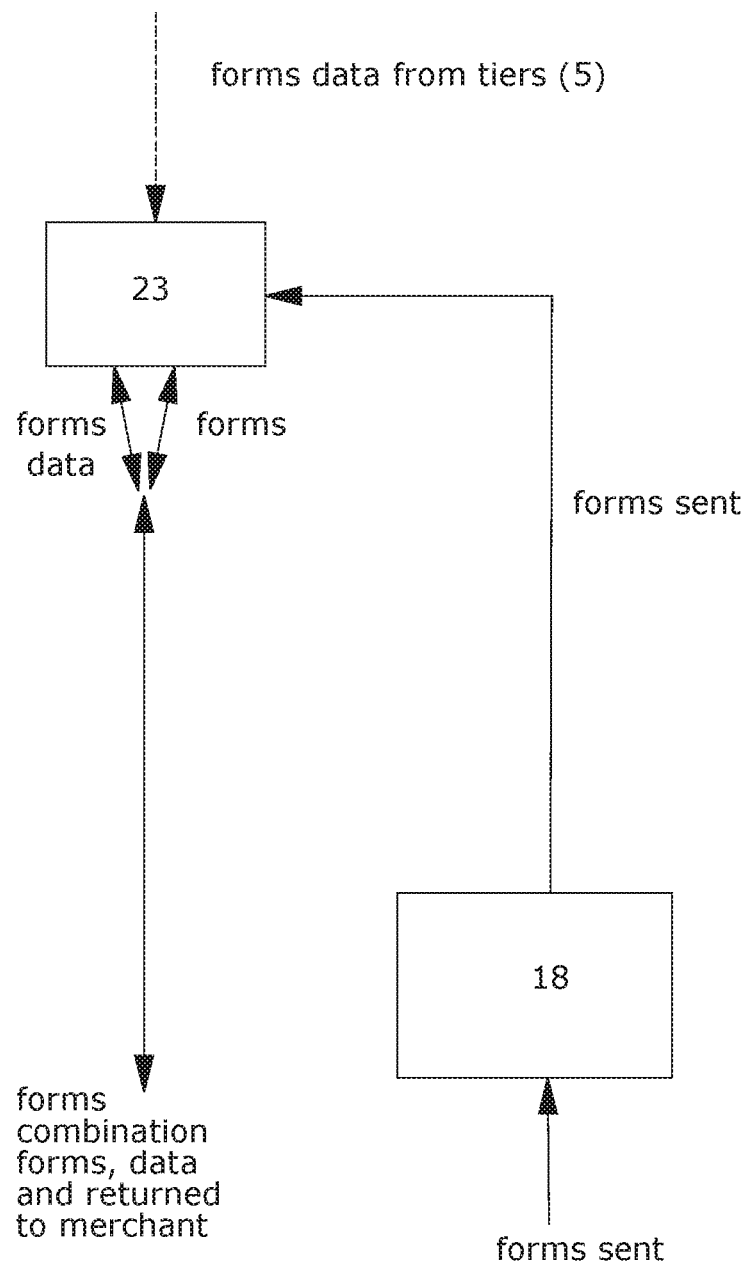
FIG. 7 shows one use of the offline forms transposer (23) in embodiments of the invention that do not have a pre-loaded forms database (20) or an on-site forms database (22).

FIG. 7 shows one use of the offline forms transposer (23) in embodiments of the invention that do not have a pre-loaded forms database (20) or an on-site forms database (22). The forms signer returns the forms data fields that the merchant was seeking to the merchant API. The merchant then selects a form, using the merchant interface, and the offline forms transposer (23) uses OCR to determine the identity of the forms data fields that match the forms data values (15) in the form, and to transpose said forms data fields into the appropriate forms data values.

In this particular example, the forms signer simply returns to the merchant everything in the tiers of which the consumer consented to release, and the consumer had previously consented to a release of all data in certain tiers.

Figure 8:
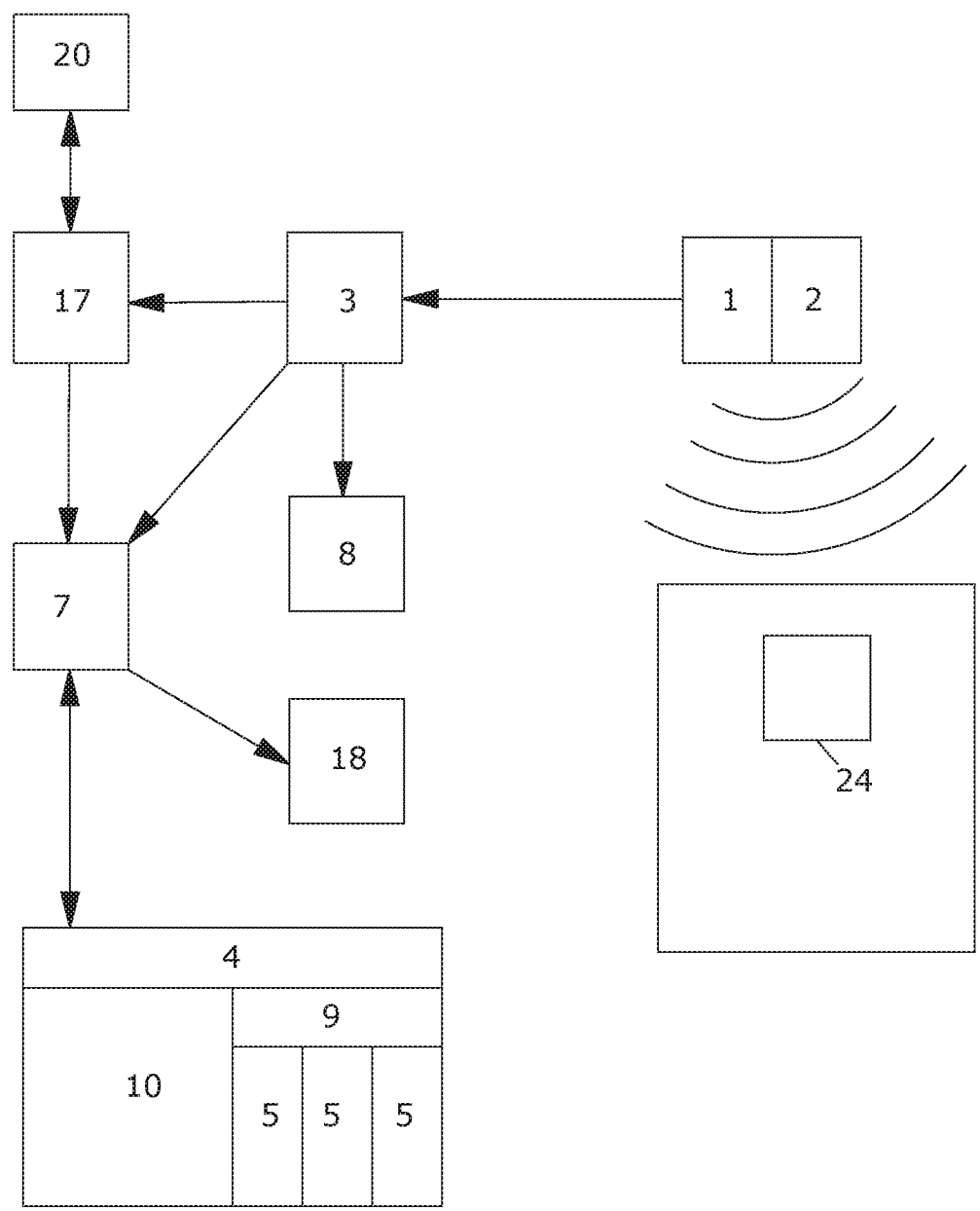
FIG. 8 shows one method of which a consumer can use a MIFI rewards mat to take advantage of an offer made by a merchant.

FIG. 8 shows one method of which a consumer can use a MIFI rewards mat to take advantage of an offer made by a merchant. The merchant also gains by gaining access to a willing consumer and the consumer's forms data more easily. First, the consumer steps on the MiFiMat. Then, the consumer takes a picture of the consumer response code (24) with the consumer device (1). Then, the picture is converted to a data stream and the data stream is sent to a transaction listener (3). The transaction listener informs the request service, notification service, and forms signer that the consumer has consented to release of his or her forms data to the merchant that created the consumer response code (24). The request service then locates the form that the merchant wanted the consumer to fill out, in the merchant's pre-loaded forms database. The request service then determines the forms data values (15) that are in that form, and communicates with the forms signer indicating which tiers of the consumer's profile the forms signer should search, based on the tiers where the forms data responsive to those forms data values will be found.

The forms signer searches the relevant tiers of the consumer's profile, and releases the responsive forms data fields to the merchant via the merchant interface (18). The merchant can then use this information later.

Figure 9:
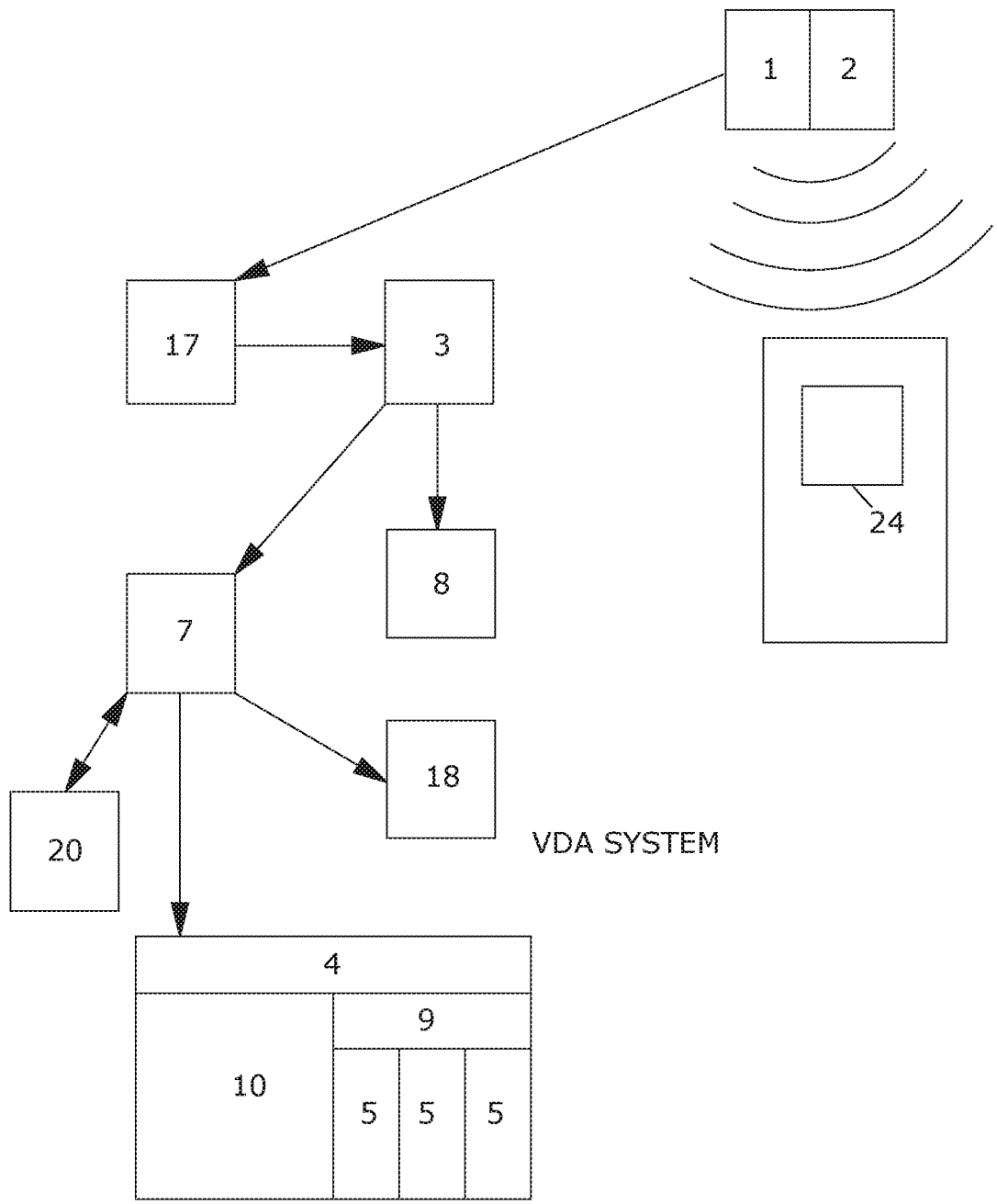
FIG. 9 shows a method by which a consumer can use the present invention to sign up for the VDA system more easily.

FIG. 9 shows a method by which a consumer can use the present invention to sign up for the Vital Data Assistant system more easily. A consumer uses the consumer program (2) on her consumer device (1) to take a picture of the consumer response code (24) on a "VDA medallion". The consumer program (2) then converts the consumer response code (24) to a data stream and sends the data stream to the request service (17). The request service (17) then creates a transaction listener and the transaction listener informs the notification service, and forms signer that the consumer has consented to release of his or her forms data to the Vital Data Assistant system.

The forms signer then locates the form that the consumer should fill out, to gain benefit from the VDA system, in the VDA system's pre-loaded forms database. The forms signer then searches the relevant tiers of the consumer's Online Profile, and sends the forms data fields that are requested by the VDA system to the VDA system, where this information is stored safely, in case the consumer ever needs it to be released to medical providers.

The invention claimed is:

1. A method of helping consumers to quickly fill out forms provided by merchants, said method comprising the steps of:
    providing a means for establishing an Online Profile (4);
        said Online Profile including a forms data storage (9);
        said forms data storage is an online database that includes one or more tiers (5);
    wherein, a consumer may use a consumer device (1) to authenticate the identity of said consumer and establish a consumer online profile; and
    wherein a consumer may use a consumer device in electronic communication with said consumer online profile to input forms data pertaining to said consumer into said forms data storage (9);
    wherein said forms data will be automatically sorted into one or more tiers (5) within said forms data storage (9) according to pre-defined sorting criteria;
    said method further comprising providing a request service and a notification service in electronic communication with said request service;
    where said request service and said notification service can both communicate over the internet;
    said method further comprising providing a pre-loaded forms database (20) within the profile of each merchant, where a merchant may save copies of forms that said merchant desires consumers to complete, where each saved form comprises forms data values that are needed to complete the form;
    said method further comprising providing that a merchant displays a consumer response code (24) to consumers;
    wherein a consumer may initiate a transaction by using a consumer interface (2), operating on a consumer device (1) to scan said consumer response code (24), and convert said consumer response code to a data stream,
    said method further comprising that said data stream will encode a unique identification code identifying a type of form belonging to the merchant displaying the consumer response code (24);
    said method further comprising that said consumer interface (2) will then send said data stream to the request service;
    said method further comprising providing a forms signer which is capable of electronically searching said one or more tiers;
    said method further comprising providing a means by which said forms signer is capable of recognizing forms data fields pertaining to the consumer, that are saved within said one or more tiers and that are responsive to the forms data values (15) within the form identified by said data stream;
    said method further comprising that either after said merchant displays said consumer response code or after said request service receives said data stream, said request service will create a transaction listener (3) which is a software component that listens for said consumer to grant authorization for consumer's forms data in said consumer online profile responsive to the forms data values in the form encoded by the data stream to be released to said merchant;
    said method further comprising said consumer electronically sending said authorization from said consumer device giving permission to the merchant for said consumer's form data saved within said one or more tiers responsive to the forms data values in the form encoded by the data stream;
    and further comprising that said transaction listener communicates said authorization to the forms signer, said request service, and said notification service, if either said request service or said transaction listener has received said authorization, of release of consumer's form data within said one or more tiers to the merchant, from said consumer;
    said method further comprising that said forms signer is in electronic communication with said request service, notification service, and any transaction listener;
    said method further comprising that said forms signer will search the pre-loaded forms database (20) for the form with the unique identification code that matches the unique identification code encoded by the data stream and forms;
    and will retrieve this form;
    said method further comprising that said forms signer will search the pre-loaded forms database for the form data values (15) pertaining to the retrieved form;
    said method further comprising that said forms signer will search some or all of the one or more tiers in said consumer's online profile's form data storage for forms data fields responsive to the forms data values (15) in the form, that the consumer has consented to fill out, encoded for by said data stream;
    and further comprising that said forms signer will import the forms data fields from the searched one or more tiers retrieved from said consumer's online profile's forms data storage into the form said forms signer retrieved from said pre-loaded forms database (20), thus either partially or fully completing said form;
    said method further comprising that said transaction listener listens for further input from said consumer and said merchant between the points when said transaction listener is created and closed;
    said method further comprising that said forms signer will electronically release said fully or partially completed form to said merchant;
    and that then said transaction listener is closed, ending the transaction.

2. The method of claim 1, further comprising that said forms signer verifies the content of the forms data fields that are sent to said merchant and that are also responsive to the forms data values (15) requested by said merchant.

3. The method of claim 1, said method further comprising that the Online Profile (4) of each consumer includes a transaction data storage (10), said transaction data storage being a database where a digital signature for each transaction by which any of the consumer's forms data is sent to a merchant;
    and said method further comprising that said forms signer stores said digital signature in said transaction data storage (10) during each transaction.

4. The method of claim 3, further comprising that said consumer response code (24) encodes the identity of the specific form, and the forms data values in said specific form, that the merchant displaying the consumer response code (24) desires the consumer to complete.

5. The method of claim 3, further comprising that said transaction listener, said request service, said notification service, and said forms signer are all located on a central server.

6. The method of claim 3, further comprising that said transaction listener, said request service, said notification service, and said forms signer are all located within a central program.

7. The method of claim 3, further comprising: before said consumer response code (24) is displayed to said consumer, said merchant send sends a request to said request service, said request containing either a unique identifying code for a form that said merchant desires said consumer to complete or the forms data values (15) needed to complete the form that said merchant desires said consumer to complete, said method further comprising before the consumer sends the consumer response code to the request service, said request service causing said notification service to electronically send a notification of the merchant's request for forms data belonging to said consumer to a consumer device (1) belonging to said consumer;

said notification requesting said consumer's permission for the forms data within specific tiers to be released to said merchant;

said method further comprising that said transaction listener (3) is created when said notification is sent to said consumer;

said method further comprising allowing said consumer to respond to said notification by the step of electronically sending a consumer response code from said consumer device (1), to said request service, giving permission for release of the forms data within said specific tiers to said merchant.

8. The method of claim 3, further comprising:

before the consumer sends the consumer response code to the request service, said merchant sends a request to said request service, said request containing either an unique identification code for the form that the merchant desires the consumer to complete, with said unique identification code also identifying the forms data values (15) in the form that the merchant desires the consumer to complete, or an identification of the forms data values (15) needed to complete the form that said merchant desires said consumer to complete, and said method further comprising that, after said request service receives the unique identification code or identification of the forms data values in the form that the merchant desires the consumer to complete, said request service to;

then displays the consumer response code (24) to said consumer, wherein, if said consumer uses said consumer interface (2) to convert said consumer response code to a data stream, said data stream includes a unique identification code for the form that the merchant desires the consumer to complete, and also identification of the forms data values (15) within said form;

and said request service also sends said consumer device (1) said notification requesting said consumer's permission for the forms data within certain specific tiers to be released to said merchant.

9. The method of claim 7, further comprising that the means for said merchant displaying the consumer response code (24) to said consumer further includes: said merchant sends a request to said request service, and said request service electronically sends to said merchant and said consumer a consumer response code (24), unique to that particular request, and said transaction listener (3) is created when said request service sends the consumer response code (24) to the merchant and the consumer, and the consumer must send the consumer response code from a consumer device (1) to the transaction listener (3) to indicate the consumer's authorization of the release of any of the forms data belonging to the consumer to the merchant.

10. The method of claim 7, further comprising that each request by any merchant for access to any consumer's forms data will have a unique transaction code (13), and further comprising that said transaction code (13) will be stored in the transaction data storage (10) for said consumer.

11. The method of claim 9, further comprising that the consumer response code (24) for each request by any merchant for access to any consumer's forms data will include data that, when converted to a data stream, encodes the identifying code of the form that the merchant wishes the consumer to complete, and also, when converted to a data stream will include data that encodes the transaction code of the particular request by that specific merchant for access to that specific consumer's forms data.

12. The method of claim 9, further comprising that the consumer response code (24) for each request by any merchant for access to any consumer's forms data will include data that, when converted to a data stream, encodes for the forms data values (15) contained in the form that the merchant wishes the consumer to complete, and said consumer response code (24) also will include data that, when converted to a data stream, encodes for the transaction code of the that particular request by that specific merchant for access to that specific consumer's forms data.

13. The method of claim 9, further comprising a consumer program (2) that includes a permission feature;

said permission feature being programmed to scan the consumer response code (24), convert the consumer response code (24) into a data stream, and electronically send the data stream to the transaction listener (3) to indicate the consumer's consent to the merchant's request for access to the consumer's forms data.

14. The method of claim 10, further comprising that when said consumer response code (24) is sent to said merchant, said forms signer sends a transaction code (13) to said consumer's consumer device, so that if said consumer does not finish said transaction, said consumer can complete the transaction later by sending said transaction code (13) to said transaction listener (3).

15. The method of claim 10, further comprising that when said request service receives a request to start a transaction from a merchant, said forms signer creates an external transaction identifier, and sends said external transaction identifier to said consumer's consumer device, at the same time as, or after, said notification service sends the notification to said consumer device (1), so that if said consumer does not finish said transaction, said consumer can complete the transaction later by sending said external transaction identifier to said transaction listener (3).

16. The method of claim 10, further comprising that the digital signature stored in the transaction data storage (10) when the forms data belonging to the consumer is sent to the merchant will include information that codes for the forms data fields that were sent to the merchant as part of the transaction.

17. The method of claim 3, further comprising that an individual may act as a consumer in some transactions, and as a merchant in other transactions.

18. The method of claim 3, further comprising that the consumer response code, when converted to a data stream, encodes for the unique identification code for the form that said merchant desires said consumer to complete, and also encodes for a transaction code (13) for that specific transaction.

19. The method of claim 3, further comprising providing a merchant interface (18), said
   merchant interface further comprising an on-site forms database (22);
   and said method further comprising that each said form in the on-site forms database will have a unique ID;
   and said method further comprising that each said form in the on-site forms database (22) can be accessed by said forms signer;
   and said method additionally comprising that said forms signer is capable of importing forms data from said forms data storage, inserting said forms data into one of said forms,
   and electronically making said completed form available via the merchant interface (18) of said merchant;
   so that when said forms signer retrieves the forms data fields responsive to the forms data values of the form that said merchant desires said consumer to fill out,
   said form signer will retrieve a copy of the form that said merchant desires said consumer to fill out from said on-site database (22) and import said forms data fields into a copy of the form that said merchant desires said consumer to fill out;
   and said forms signer will then deliver said completed form to the merchant interface (18) of said merchant.

20. The method of claim 10, further comprising that said transaction ID is authenticated with a hashtag.

21. The method of claim 1,
   further comprising that said consumer response code (24) is displayed on a mat.

22. The method of claim 1, further comprising
   that said consumer response code (24) is displayed on a VDA medallion
   unique identification code of a type of form belonging to the merchant that the VDA medallion.

23. The method of claim 17, further comprising that a first individual and a second individual may quickly exchange forms data with each other by the following steps:
   each said individual creates an Online Profile (4), and uploads forms data into the tiers (5) of said online profile (4);
   each said individual uploads forms into the pre-loaded forms database (20),
   and said method further comprising that said first individual then displays one or more consumer response codes (24) to the second individual, where the second individual may scan each consumer response code, received from the first individual, to initiate a separate transaction,
   and that said second individual then displays one or more consumer response codes (24) to the first individual, where the first individual may scan each consumer response code, received from the first individual, to initiate another separate transaction.

\* \* \* \* \*